(12) United States Patent
Thrue et al.

(10) Patent No.: US 8,357,670 B2
(45) Date of Patent: Jan. 22, 2013

(54) OLIGOMERIC COMPOUNDS FOR THE MODULATION OF HIF-1A EXPRESSION

(75) Inventors: Charlotte Albaek Thrue, Copenhagen K (DK); Anja Molhart Hog, Vium (DK); Paul E. G. Kristjansen, Horsholm (DK)

(73) Assignees: Enzon Pharmaceuticals, Inc., Piscataway, NJ (US); Santaris Pharama A/S, Horsholm (DK)

( * ) Notice: Subject to any disclaimer, the term of this patent is extended or adjusted under 35 U.S.C. 154(b) by 0 days.

(21) Appl. No.: 13/477,825

(22) Filed: May 22, 2012

(65) Prior Publication Data
US 2012/0270924 A1 Oct. 25, 2012

Related U.S. Application Data

(60) Division of application No. 12/913,173, filed on Oct. 27, 2010, now Pat. No. 8,207,140, which is a continuation of application No. 12/580,126, filed on Oct. 15, 2009, now Pat. No. 7,846,911, which is a division of application No. 10/407,807, filed on Apr. 4, 2003, now Pat. No. 7,737,264.

(60) Provisional application No. 60/370,126, filed on Apr. 5, 2002.

(51) Int. Cl.
*A16K 48/00* (2006.01)
(52) U.S. Cl. ...... 514/44; 536/24.5; 536/24.1; 536/24.31
(58) Field of Classification Search ........................ None
See application file for complete search history.

(56) References Cited

U.S. PATENT DOCUMENTS

| 4,857,653 A | 8/1989 | Colin et al. |
| 5,108,921 A | 4/1992 | Low et al. |
| 5,227,400 A | 7/1993 | Holton et al. |
| 5,248,796 A | 9/1993 | Chen et al. |
| 5,250,683 A | 10/1993 | Holton et al. |
| 5,254,580 A | 10/1993 | Chen et al. |
| 5,272,171 A | 12/1993 | Ueda et al. |
| 5,278,324 A | 1/1994 | Kingston et al. |
| 5,595,760 A | 1/1997 | Cherif-Cheikh |
| 5,672,659 A | 9/1997 | Shalaby et al. |
| 5,801,154 A | 9/1998 | Baracchini et al. |
| 5,882,914 A | 3/1999 | Semenza |
| 5,994,076 A | 11/1999 | Chenchik et al. |
| 6,030,954 A | 2/2000 | Wu et al. |
| 6,706,505 B1 | 3/2004 | Han et al. |
| 6,770,748 B2 | 8/2004 | Imanishi et al. |
| 6,821,724 B1 | 11/2004 | Mittman et al. |
| 2003/0003092 A1* | 1/2003 | Krissansen et al. .......... 424/94.1 |
| 2003/0032794 A1 | 2/2003 | Koch et al. |
| 2004/0002473 A1 | 1/2004 | Kurreck et al. |
| 2004/0220393 A1 | 11/2004 | Ward et al. |

FOREIGN PATENT DOCUMENTS

| EP | 0253739 | 10/1989 |
| WO | WO92/09589 | 6/1992 |
| WO | WO93/18210 | 9/1993 |
| WO | WO96/39426 | 12/1996 |
| WO | WO99/14226 | 3/1999 |
| WO | WO99/48916 | 9/1999 |
| WO | WO99/49065 | 9/1999 |
| WO | WO00/12548 | 9/2000 |
| WO | WO00/54746 | 9/2000 |
| WO | WO00/56748 | 9/2000 |
| WO | WO00/64262 | 11/2000 |
| WO | WO00/66604 | 11/2000 |
| WO | WO00/76497 | 12/2000 |
| WO | WO00/78341 | 12/2000 |
| WO | WO01/19505 | 3/2001 |
| WO | WO01/25248 | 4/2001 |
| WO | WO03/006475 | 1/2002 |
| WO | WO02/28875 | 4/2002 |
| WO | WO02/34291 | 5/2002 |
| WO | WO02/094250 | 11/2002 |
| WO | WO02/099104 | 12/2002 |
| WO | WO03/085110 | 10/2003 |
| WO | WO03/095467 | 11/2003 |
| WO | WO2004/042024 | 5/2004 |
| WO | WO2004/046160 | 6/2004 |
| WO | WO2004/069991 | 8/2004 |
| WO | WO2004/069992 | 8/2004 |

OTHER PUBLICATIONS

Acheampong et al., 2002, "Distribution of Brimonidine into Anterior and Posterior Tissues of Monkey, Rabbit, and Rat Eyes," Drug Metabolism and Distribution, 30(4):421-429.
Andrew Chin, "On the Preparation and Utilization Isolated and Purified Oligonucleotides", University of North Carolina School of Law, Mar. 9, 2002.
Andrew, et al., "Nickel requires hypoxia-inducible factor-1.alpha., not redox signaling, to induce plasminogen activator inhibitor-1," Am J. Physiol. Lung Cell Mol Physiol, vol. 281, pp. L607-L615, 2001.
Beaucage et al., 1992, "Advances in the Synthesis of Oligonucleotides by the Phosphoramidite Approach," Tetrahedron, 48(12):2223-2311.
Beaucage et al., 1993, "The Synthesis of Modified Oligonucleotides by the Phosphoramidite Approach and Their Applications," Tetrahedron, 49(28):6123-6194.
Brown et al., 1991, "In Oligonucleotides and Analogues. A Practical Approach," Oxford: IRL 13-14.

(Continued)

*Primary Examiner* — Kimberly Chong
(74) *Attorney, Agent, or Firm* — Stoel Rives LLP

(57) ABSTRACT

Oligonucleotides directed against the hypoxia-inducible factor-1α (HIF-1α) gene are provided for modulating the expression of HIF-1α. The compositions comprise oligonucleotides, particularly antisense oligonucleotides, targeted to nucleic acids encoding the HIF-1α. Methods of using these compounds for modulation of HIF-1α expression and for the treatment of diseases associated with the hypoxia-inducible factor-1α are provided. Examples of diseases are cancer and pre-eclampsia. The oligonucleotides may be composed of deoxyribonucleosides, a nucleic acid analogue, or Locked Nucleic Acid (LNA) or a combination thereof.

9 Claims, 10 Drawing Sheets

OTHER PUBLICATIONS

Caniggia, I., et al., "Oxygen and Placental Development During the First Trimester: Implications for the Pathophysiology of Pre-eclampsia," Placenta, 21, Supplement A, Trophoblast Research 14, pp. S25-S30, 2000.

Caniggia, et al., "Hypoxia-inducible factor-1 mediates the biological effects of oxygen on human trophoblast differentiation through TGF. beta..sub.3 " The Journal of Clinical Investigation, vol. 105, No. 5, pp. 577-587, 2000.

Cao et al., 1998, "Vascular Endothelial Growth Factor C Induces Angiogenesis in vivo," Proc. Nat. Acad. Sci., 95(24):14389-14394.

Crooke, R.M., 1997, "In Vitro Cellular Uptake, Distribution, and Metabolism of Oligonucleotides," Antisense Res. and Application 131:103-140.

Dai et al., 2003, "Inhibition of Hypoxia Inducible Factor 1.alpha. Causes Oxygen-Independent Cytotoxicity and Induces p53 Independent Apoptosis in Glioblastoma Cells," Int J. Radiat Oncol Biol Phys., 55(4):1027-1036.

Dass, Crispin R., 2002, "Vehicles for Oligonucleotide Delivery to Tumours," J Pharm Pharmacol., 54(1):3-27.

Distler et al., 2004, "Physiologic Responses to Hypoxia and Implications for Hypoxia-Inducible Factors in the Pathogenesis of Rheumatoid Arthritis," Arthritis Rheum., 50(1):10-23.

Drutel, et al., "Two splice variants of the hypoxia-inducible factor HIF-1.alpha. as potential dimerization partners of ARNT2 in neurons," European Journal of Neuroscience, vol. 12, pp. 3701-3708, 2000.

Freier, et al., "The ups and downs of nucleic acid duplex stability: structure-stability studies on chemically-modified DNA:RNA duplexes," Nucleic Acids Research, vol. 25, No. 22, pp. 4429-4443, 1997.

Heid et al., 1996, "Real time Quantitative PCR," Genome Res., 6(10):986-994.

Hoeg, et al., 2002, "Specific down-regulation of hypoxia-inducible factor 1.alpha. (HIF1.alpha.) in a human glioblastoma cell line by locked nucleic acid (LNA) antisense oli-gonucleotides," American Association for cancer Research, #4763, vol. 43:962.

Holmes et al., 1991, "Phase II Trial of Taxol, an Active Drug in the Treatment of Metastatic Breast Cancer," J. Natl. Cancer Inst., 83(24)1797-1805.

Holton et al., 1994, "First Total Synthesis of Taxol. 1. Functionalization of the B Ring," J. Am. Chem. Soc., 116(4):1597-1598.

International Preliminary Report on Patentability dated Apr. 7, 2010 corresponding to International Application No. PCT/EP2008/062658.

Kakinuma, Y., et al., "Novel Molecular Mechanism of Increased Myocardial Endothelin-1 Expression in the Failing Heart Involving the Transcriptional Factor Hypoxia-Inducible Factor-1.alpha. Induced for Impaired Myocardial Energy Metabolism," Circulation, vol. 103, pp. 2387-2394, 2001.

Kang et al., 2001, "An Antisense Oligonucleotide That Inhibits the Expression of Hypoxia-Inducible Factor-1.alpha. Alters Hypoxia-Induced Changes in Proliferation and Viability of Human Cardiac Fibroblasts," Basic Science/Schientific Sessions, II-57:274.

Kang et al., Circulation, American Heart Associatio, vol. 104, No. 17, Suppl., pp. 1157 (2001), Database No. XP009015505.

Kohn et al., 1994, "Dose-Intense Taxol: High Response Rate in Patients With Platinum-Resistant Recurrent Ovarian Cancer," J. Natl. Cancer Inst., 86(1)18-24.

Koshkin et al. LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition. Tetrahedron 1998, vol. 54: 3607-3630. Elsevier Science Ltd.

Koshkin, et al., "A Simplified and Efficient Route to 2'-0, 4'-C-Methylene-Linked Bicyclic Ribonucleosides (Locked Nucleic Acid)," J. Org. Chem., vol. 66, pp. 8504-8512, 2001.

Kurreck et al. Design of antisense oligonucleotides stabilized by locked nucleic acids. Nucleic Acids Research 2002, Vo. 30. No. 9: 1911-1918.

L'Allemain, Bull. Cancer, vol. 89, No. 3, pp. 257-260 (2002), Abstract Only—No Translation.

Leamon et al., 1991, "Delivery of Macromolecules into Living Cells: A Method that Exploits Folate Receptor Endocytosis," Proc. Nat. Acad. Sci., 88:5572-5576.

Maxwell, P. The HIF Pathway in cancer. Seminars in Cell & Dev. Biology 2005, pp. 523-530. cited by examiner.

McGuire et al., "Taxol: A Unique Antineoplastic Agent with Significant Activity in Advanced Ovarian Epithelial Neoplasms." Ann. Intern. Med. vol. 111, pp. 273-279 (1989).

Narravula, et al., "Hypoxia-Inducible Factor 1-Mediated Inhibition of Peroxisome Proliferator-Activated Receptor .alpha. Expression During Hypoxia," The Journal of Immunology, vol. 166: pp. 7543-7548, 2001.

Nicolaou et al., 1994, "Total Synthesis of Taxol," Nature 367:630-634.

Notice of Allowance received in U.S. Appl. No. 10/407,807 dated Jul. 20, 2009.

Notice of Allowance received in U.S. Appl. No. 12/580,126 dated Jul. 27, 2010.

Notice of Allowance received in U.S. Appl. No. 12/913,173 dated Feb. 22, 2012.

Office Action received in U.S. Appl. No. 10/407,807 dated Jul. 20, 2005.

Office Action received in U.S. Appl. No. 10/407,807 dated Sep. 11, 2006.

Office Action received in U.S. Appl. No. 10/407,807 dated Jul. 26, 2007.

Office Action received in U.S. Appl. No. 10/407,807 dated Apr. 14, 2008.

Office Action received in U.S. Appl. No. 10/407,807 dated Oct. 30, 2008.

Office Action received in U.S. Appl. No. 10/407,807 dated May 21, 2009.

Office Action received in U.S. Appl. No. 12/580,126 dated Feb. 5, 2010.

Office Action received in U.S. Appl. No. 12/913,173 dated Sep. 20, 2011.

Paul et al., 2004, "HIF at the Crossroads Between Ischemia and Carcinogenesis," J. Cell. Physiol., 200(1):20-30.

Pedersen et al., 2002, "Preparation of LNA Phosphoramidites," Synthesis 2000(6):802-808.

Poulaki et al., 2003, "Regulation of Vascular Endothelial Growth Factor Expression by Insulin-Like Growth Factor I in Thyroid Carcinomas," J. Clin. Endocrinol. Metab., 88(11):5392-5398.

Poulaki et al., 2004, "Insulin-Like Growth Factor-I Plays a Pathogenetic Role in Diabetic Retinopathy," Am. J. Pathology, 165(2):457-469.

Preliminary Amendment filed Jan. 28, 2004 in U.S. Appl. No. 10/407,807.

Response to Restriction Requirement filed Jun. 20, 2005 in U.S. Appl. No. 10/407,807.

Response to Office Action filed Dec. 19, 2005 in U.S. Appl. No. 10/407,807.

Response to Office Action and RCE filed Feb. 9, 2007 in U.S. Appl. No. 10/407,807.

Response to Office Action filed Dec. 21, 2007 in U.S. Appl. No. 10/407,807.

Response to Office Action filed Jun. 9, 2008 in U.S. Appl. No. 10/407,807.

Response to Office Action and RCE filed Aug. 1, 2008 in U.S. Appl. No. 10/407,807.

Response to Office Action filed Jan. 29, 2009 in U.S. Appl. No. 10/407,807.

Response to Office Action filed Jun. 11, 2009 in U.S. Appl. No. 10/407,807.

Response to Office Action filed Apr. 28, 2010 in U.S. Appl. No. 12/580,126.

Response to Pre Exam Formalities Notice filed Nov. 20, 2009 in U.S. Appl. No. 12/580,126.

Response to Office Action filed Dec. 9, 2012 in U.S. Appl. No. 12/913,713.

Restriction Requirement received in U.S. Appl. No. 10/407,807 dated Apr. 18, 2005.

Rosenbohm, et al., "Synthesis of 2'-amino-LNA: a new strategy," Org. Biomol. Chem., vol. 1, pp. 655-663, 2003.

Semenza, G. Targeting HIF-1 for cancer therapy. Nature Reviews Cancer, vol. 3, Oct. 2003, pp. 721-732.

Shatrov et al., 2003, "Oxidized Low-Density Lipoprotein (oxLDL) Triggers Hypoxia-Inducible Factor-1.alpha. (HIF-1.alpha.) Accumulation via Redox-Dependent Mechanisms," Blood, 101(12):4847-4849.

Sorensen, et al., ".alpha.-L-ribo-Configured Locked Nucleic Acid (.alpha.—L-LNA): Synthesis and Properties," J. Am. Chem. Soc., vol. 124, No. 10, pp. 2164-2176, 2002.

Streilein et al., 1996, "Immunosuppressive Properties of Tissues Obtained from Eyes with Experimentally Manipulated Corneas," Investigative Ophthalmology & Visual Science, 37(2):413-424.

Sun et al., 2003, "Regression of Solid Tumors by Engineered Overexpression of von Hippel—Lindau Tumor Suppressor Protein and Antisense Hypoxia-Inducible Factor-1.alpha.," Gene Therapy, 10:2081-2089.

Sun, 2001, "Gene Transfer of Antisense Hypoxia Inducible Factor-1.alpha. Enhances the Therapeutic Efficacy of Cancer Immunotherapy," Gene Therapy, 8(8):638-645.

Talks, et al., "The Expression and Distribution of the Hypoxia-Inducible Factors HIF-1.alpha. and HIF-2.alpha. in Normal Human Tissues, Cancers, and Tumor-Associated Macrophages," American Journal of Pathology, vol. 157, No. 2, pp. 411-421, 2000.

Uhlmann, Eugen, "Recent advances in the medicinal chemistry of antisense Oligonucleotides," Curr. Opinion in Drug & Development, vol. 3, No. 2, pp. 203-213 (2000).

Venetsanakos et al., 2002, "Induction of Tubulogenesis in Telomerase-Immortalized Human Microvascular Endothelial Cells by Glioblastoma Cells," Exp. Cell. Res., 273(1):21-33.

Wagner et al., 1990, "Transferrin-Polycation Conjugates as Carriers for DNA Uptake into Cells," Proc. Nat. Acad. Sci., 87:3410-3414.

Wang et al., 2003, "Bimodal Effect of Hypoxia in Cancer: Role of Hypoxia Inducible Factor in Apoptosis," Mol. Pharmaceutics, 1(2):156-165.

Wrone-Smith et al., 1996, "Dermal Injection of Immunocytes Induces Psoriasis," J. Clin. Invest., 98(8):1878-1887.

Zhang et al., 2004, "Treatment with siRNA and Antisense Oligonucleotides Targeted to HIF-1.alpha. Induced Apoptosis in Human Tongue Squamous Cell Carcinomas," Int. J. Cancer, 111(6):849-857.

Zhong, et al., "Overexpresssion of Hypoxia-inducible Factor 1.alpha. in Common Human Cancers and Their Metastases," Cancer Research, vol. 59, pp. 5830-5835, 1999.

* cited by examiner

Western blot
Oligo concentration 200 nM

Oligo concentration 200 nM

Western blot
Mismatch oligos

Western blot
U373
6 hours treatment with 100 nM oligonucleotide
20 hours anoxia

Screening of gene-walk oligos

B : Cur813 5mg/kg/day, i.p. x 1 daily for 7 days
A: PBS, 100μl/10g/day, i.p. x1 daily for 7 days

Figure 10

SEQ ID NO 1
```
   1 cacgaggcag cactctcttc gtcgcttcgg ccagtgtgtc gggctgggcc ctgacaagcc
  61 acctgaggag aggctcggag ccgggccngg accccggcga ttgccgcccg cttctctcta
 121 gtctcacgag gggtttcccg cctcgcaccc ccacctctgg acttgccttt ccttctcttc
 181 tccgcgtgtg gagggagcca gcgcttaggc cggagcgagc ctggggggccg cccgccgtga
 241 agacatcgcg gggaccgatt caccatggag ggcgccggcg gcgcgaacga caagaaaaag
 301 ataagttctg aacgtcgaaa agaaaagtct cgagatgcag ccagatctcg gcgaagtaaa
 361 gaatctgaag tttttttatga gcttgctcat cagttgccac ttccacataa tgtgagttcg
 421 catcttgata aggcctctgt gatgaggctt accatcagct atttgcgtgt gaggaaactt
 481 ctggatgctg gtgatttgga tattgaagat gacatgaaag cacagatgaa ttgcttttat
 541 ttgaaagcct tggatggttt tgttatggtt ctcacagatg atggtgacat gatttacatt
 601 tctgataatg tgaacaaata catgggatta actcagtttg aactaactgg acacagtgtg
 661 tttgatttta ctcatccatg tgaccatgag gaatgagag aatgcttac acacagaaat
 721 ggccttgtga aaaagggtaa agaacaaaac acacagcgaa gcttttttct cagaatgaag
 781 tgtaccctaa ctagccgagg aagaactatg aacataaagt ctgcaacatg gaaggtattg
 841 cactgcacag gccacattca cgtatatgat accaacagta accaacctca gtgtgggtat
 901 aagaaaccac ctatgacctg cttggtgctg atttgtgaac ccattcctca cccatcaaat
 961 attgaaattc ctttagatag caagactttc ctcagtcgac acagcctgga tatgaaattt
1021 tcttattgtg atgaaagaat taccgaattg atgggatatg agccagaaga acttttaggc
1081 cgctcaattt atgaatatta tcatgctttg gactctgatc atctgaccaa aactcatcat
1141 gatatgttta ctaaaggaca agtcaccaca ggacagtaca ggatgcttgc caaaagaggt
1201 ggatatgtct gggttgaaac tcaagcaact gtcatatata acaccaagaa ttctcaacca
1261 cagtgcattg tatgtgtgaa ttcgttgtg agtggtatta ttcagcacga cttgattttc
1321 tcccttcaac aaacgaatg tgtccttaaa ccggttgaat cttcagatat gaaaatgact
1381 cagctattca ccaaagttga atcagaagat acaagtagcc tctttgacaa acttaagaag
1441 gaacctgatg ctttaacttt gctggcccca gccgctggag acacaatcat atctttagat
1501 tttggcagca acgacacaga aactgatgac cagcaacttg aggaagtacc attatataat
1561 gatgtaatgc tcccctcacc caacgaaaaa ttacagaata taaatttggc aatgtctcca
1621 ttacccaccg ctgaaacgcc aaagccactt cgaagtagtg ctgaccctgc actcaatcaa
1681 gaagttgcat taaaattaga accaaatcca gagtcactgg aacttttcttt taccatgccc
1741 cagattcagg atcagacacc tagtccttcc gatggaagca ctagacaaag ttcacctgag
1801 cctaatagtc ccagtgaata ttgtttttat gtggatagtg atatggtcaa tgaattcaag
1861 ttggaattgg tagaaaaact ttttgctgaa gacacagaag caaagaaccc attttctact
1921 caggacacag atttagactt ggagatgtta gctccctata tcccaatgga tgatgacttc
1981 cagttacgtt ccttcgatca gttgtcacca ttagaaagca gttccgcaag ccctgaaagc
2041 gcaagtcctc aaagcacagt tacagtattc cagcagactc aaatacaaga acctactgct
2101 aatgccacca ctaccactgc caccactgat gaattaaaaa cagtgacaaa agaccgtatg
2161 gaagacatta aatattgat tgcatctcca tctcctaccc acatacataa agaaactact
2221 agtgccacat catcaccata tagagatact caaagtcgga cagcctcacc aaacagagca
2281 ggaaaaggag tcatagaaca gacagaaaaa tctcatccaa gaagcccctaa cgtgttatct
2341 gtcgctttga gtcaaagaac tacagttcct gaggaagaac taaatccaaa gatactagct
2401 ttgcagaatg ctcagagaaa gcgaaaaatg gaacatgatg gttcactttt tcaagcagta
2461 ggaattggaa cattattaca gcagccagac gatcatgcag ctactacatc actttcttgg
2521 aaacgtgtaa aaggatgcaa atctagtgaa cagaatggaa tggagcaaaa gacaattatt
2581 ttaatacct ctgatttagc atgtagactg ctggggcaat caatggatga agtggatta
2641 ccacagctga ccagttatga ttgtgaagtt aatgctccta caaggcag cagaaaccta
2701 ctgcagggtg aagaattact cagagctttg gatcaagtta actgagcttt tccttaattt
2761 cattccttttt tttggacact ggtggctcac tacctaaagc agtctattta tattttctac
2821 atctaatttt agaagcctgg ctacaatact gcacaaactt ggttagttca attttttgatc
2881 cccttctac ttaatttaca ttaatgctct ttttagtat gttcttttaat gctggatcac
2941 agacagctca tttttctcagt tttttggtat taaaccatt gcattgcagt agcatcattt
3001 taaaaatgc acctttttat ttatttatt ttggctaggg agtttatccc ttttttcgaat
3061 tatttttaag aagatgccaa tataattttt gtaagaaggc agtaaccttt catcatgatc
3121 ataggcagtt gaaaaatttt tacaccttt ttttcacatt ttacataaat aataatgctt
3181 tgccagcagt acgtggtagc cacaattgca caatatattt tcttaaaaaa taccagcagt
3241 tactcatgga atatattctg cgtttataaa actagttttt aagaagaaat ttttttttggc
3301 ctatgaaatt gttaaacctg gaacatgaca ttgttaatca tataataatg attcttaaat
3361 gctgtatggt ttattattta aatgggtaaa gccatttaca taatataaa agatatgcat
3421 atatctagaa ggtatgtggc atttatttgg ataaaattct caattcagag aaatcatctg
3481 atgtttctat agtcactttg ccagctcaaa agaaaacaat accctatgta gttgtggaag
3541 tttatgctaa tattgtgtaa ctgatattaa acctaaatgt tctgcctacc ctgttggtat
3601 aaagatattt tgagcagact gtaaacaaga aaaaaaaaat catgcattct tagcaaaatt
3661 gcctagtatg ttaatttgct caaaatacaa tgtttgattt tatgcacttt gtcgctatta
3721 acatcctttt tttcatgtag atttcaataa ttgagtaatt ttagaagcat tatttttagga
3781 atatatagtt gtcacagtaa atatcttgtt ttttctatgt acattgtaca aattttttcat
3841 tccttttgct ctttgtggtt ggatctaaca ctaactgtat tgttttgtta catcaaataa
3901 acatcttctg tggaaaaaaa aaaaaaaaaa aaa
```

OLIGOMERIC COMPOUNDS FOR THE MODULATION OF HIF-1A EXPRESSION

CROSS-REFERENCE TO RELATED APPLICATIONS

The present application is a divisional of U.S. patent application Ser. No. 12/913,173 which is a continuation of U.S. patent application Ser. No. 12/580,126 filed on Oct. 15, 2009, which issued as U.S. Pat. No. 7,846,911 on Dec. 7, 2010, which is a divisional of U.S. patent application Ser. No. 10/407,807 filed on Apr. 4, 2003, which issued as U.S. Pat. No. 7,737,264 on Jun. 15, 2010 which claims the benefit under 35 U.S.C. §119(e) of U.S. Provisional Application Ser. No. 60/370,126, filed on Apr. 5, 2002, each of which is incorporated herein by reference in its entirety.

FIELD OF THE INVENTION

The present invention provides compositions and methods for modulating the expression of HIF-1α. In particular, this invention relates to oligomeric compounds and preferred such compounds are oligonucleotides, which are specifically hybridisable with nucleic acids encoding HIF-1α. The oligonucleotide compounds have been shown to modulate the expression of HIF-1α and pharmaceutical preparations thereof and their use as treatment of cancer diseases and pre-eclampsia are disclosed.

BACKGROUND OF THE INVENTION

Solid tumors must establish a blood supply and have enhanced glucose metabolism to grow beyond a few millimeters. How they sense hypoxia, and respond by activating hypoxia-inducible genes and secreting angiogenic factors to establish a blood system is central to cancer biology. Many tumors contain hypoxic microenvironments, which have been associated with malignant progression, metastasis and resistance to radiotherapy and chemotherapy.

The discovery of hypoxia-inducible factor-1 (HIF-1) gave some insight into the regulation of hypoxia-inducible genes (U.S. Pat. No. 5,882,914 and WO9639426; WO9948916). HIF-1 is composed of two subunits HIF-1α and HIF-1β and it binds hypoxia-response elements (HREs) in enhancers of genes encoding angiogenic factors such as VEGF and glycolysis-related proteins such as glycolytic enzymes and glucose transporter 1 and 3 (GLU-1 and 3).

It has been demonstrated that engineered down-regulation of HIF-1α by intratumoral gene transfer of an antisense HIF-1α plasmid leads to the down-regulation of VEGF, and decreased tumor microvessel density (WO 0076497, Sun X et al, Gene Therapy (2001) 8, 638-645). The plasmid contained a 320-bp cDNA fragment encoding 5'-end of HIF-1α (nucleotides 152-454; Genebank AF003698). Furthermore, in the International Patent Application cited above a method was described based on that the expression vector should be used in conjunction with an immunotherapeutic agent. However, a major weakness with the expression plasmid approach is that it will not be suitable as a therapeutic agent due to its size and the nuclease sensitivity of the expression product.

Besides the plasmid expressing a HIF-1α fragment a few antisense oligonucleotides targeting HIF-1α have been designed as research tools to study a specific biological mechanism or biological target. For example the antisense inhibition of HIF-1α expression in hypoxic explants have been shown to inhibit expression of TGFβ (Caniggia, I., et al J. of Clinical Investigation, March 2000, 105, 577-587). In this particular study, only one antisense oligonucleotide was synthesized, a phosphorothioate targeted against the sequence adjacent to the AUG initiation codon of HIF-1α mRNA. The sequences were HIF-1α 5'-GCCGGCGCCCTC-CAT-3' and the HIF-1α down regulation was demonstrated at mRNA level. This oligo has been used to study the role of HIF-1α in extravillous trophoblast outgrowth and invasion, and implicated at potential role of HIF-1α in pre-eclampsia (Caniggia, I. et al Placenta (2000), 21, Supplement A, Trophoblast Research 14, S25-S30).

Another study, using the same oligonucleotide sequence as above, showed that antisense inhibition of HIF-1α resulted in loss of peroxisome proliferator-active receptors (PPARs) (Narravula, S, and Colgan S. P., J. of Immunology, 2001, 166, 7543-7548). The above mentioned oligo has also been used to show that nickel requires HIF-1α to induce plasminogen activator inhibitior-1 (PAI-1) (Andrew, A. S. Klei L. R., Barchowsky A, Am. J. Physiol. Lung Cell Mol. Physiol. 281, L607-L615, 2001).

A single antisense oligonucleotide has also been used to study the two splice variants of the hypoxia-inducible factor HIF-1α as potential dimerization partner of ARNT2 in neurons. The antisense oligonucleotide was the phosphorothioate-modification of the sequence: 5'-TCTTCTCGT-TCTCGCC-3'. Treating cells with this oligonucleotide resulted in inhibition of [³H]thymidine incorporation, but did not have an effect on apoptosis in normoxic cells (Drutel et. al. (2000) Eur. J. Neurosci. 12, 3701-3708).

Furthermore, a single antisense oligonucleotide for HIF-1α have been showed to inhibit the increased gene expression of cardiac endothelin (ET)-1 and it was hypothesized that HIF-1α is involved in increased myocardial expression of the ET-1 gene in heart failure (Kakinuma, Y. et al, Circulation, 2001; 103, 2387-2394). The antisense oligonucleotide had the following sequence: CCTCCATGGCGAATCGGTGC.

Currently, there are no known therapeutic antisense agents, which effectively inhibit the synthesis of HIF-1α and which can be used for the treatment of a disease. Consequently, there is a need for agents capable of effectively inhibiting the HIF-1α function to be used in the treatment of e.g. cancer and pre-eclampsia.

SUMMARY OF THE INVENTION

The present invention is directed to oligomeric compounds, particularly LNA antisense oligonucleotides, which are targeted to a nucleic acid encoding HIF-1α and which modulate the expression of the HIF-1α. Pharmaceutical and other compositions comprising the oligomeric compounds of the invention are also provided. Further provided are methods of modulating the expression of HIF-1α in cells or tissues comprising contacting said cells or tissues with one or more of the oligomeric compounds or compositions of the invention. Also disclosed are methods of treating an animal or a human, suspected of having or being prone to a disease or condition, associated with expression of HIF-1α by administering a therapeutically or prophylactically effective amount of one or more of the oligomeric compounds or compositions of the invention. Further, methods of using oligomeric compounds for the inhibition of expression of HIF-1α and for treatment of diseases associated with these HIF-1α are provided. Examples of such diseases are different types of cancer, particularly common cancers, as e.g. primary and metastatic breast, colorectal, prostate, pancreas, other GI-cancers, lung, cervical, ovarian, and brain tumors, as well as pre-eclampsia, inflammatory bowel disease and Alzheimers disease. Other examples are cancer of the colon, liver, thyroid, kidney, testes, stomach, intestine, bowel, esophagus, spinal cord, sinuses, bladder or urinary tract.

BRIEF DESCRIPTION OF THE FIGURES

FIG. 10 shows human. HIF-1α sequence, using GenBank accession number NM_001530, incorporated herein as SEQ ID NO:1.

DEFINITION

Figure 1:
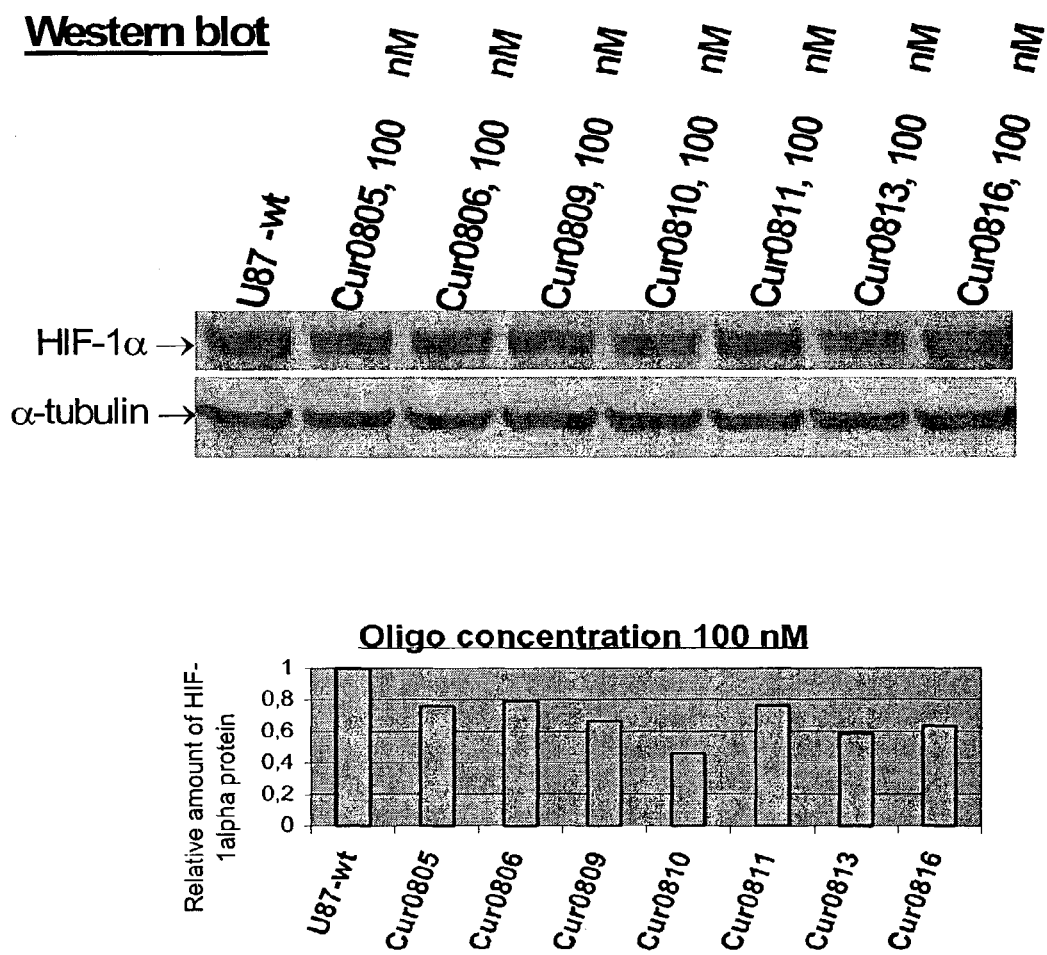
FIG. 1 shows a Western blot of HIF-1α protein. Cells were treated with the different oligos at 100 nM for 4 hours. The cells were allowed to grow for 18 hours before they were exposed to severe hypoxia for 6 hours.
Figure 2:
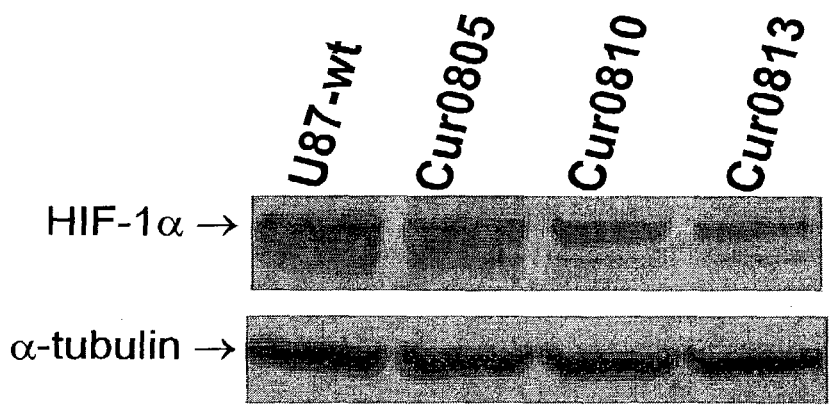
FIG. 2 shows a Western blot of HIF-1α protein. U87 cells were treated with three of the oligos at 200 nM for 4 hours. The cells were exposed to severe hypoxia for 18 hours immediately after the treatment.
Figure 2:
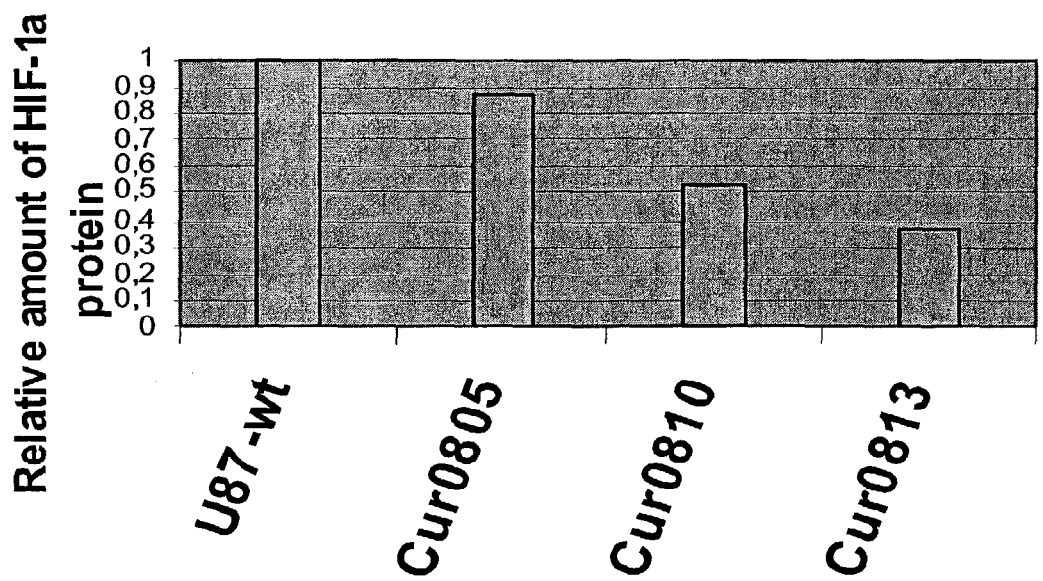

As used herein, the terms "target nucleic acid" encompass DNA encoding the hypoxia-inducible factor or encoding hypoxia-inducible factor-1α (HIF-1α), RNA (including pre-mRNA and mRNA) transcribed from such DNA, and also cDNA derived from such RNA.

As used herein, the term "gene" means the gene including exons, introns, non-coding 5' and 3' regions and regulatory elements and all currently known variants thereof and any further variants, which may be elucidated.

As used herein, the terms "oligomeric compound" refers to an oligonucleotide which can induce a desired therapeutic effect in humans through for example binding by hydrogen bonding to either a target gene "Chimeraplast" and "TFO", to the RNA transcript(s) of the target gene "antisense inhibitors", "siRNA", "ribozymes" and oligozymes" or to the protein(s) encoding by the target gene "aptamer", spiegelmer" or "decoy".

As used herein, the term "mRNA" means the presently known mRNA transcript(s) of a targeted gene, and any further transcripts, which may be identified.

As used herein, the term "modulation" means either an increase (stimulation) or a decrease (inhibition) in the expression of a gene. In the present invention, inhibition is the preferred form of modulation of gene expression and mRNA is a preferred target.

As used herein, the term "targeting" an antisense compound to a particular target nucleic acid means providing the antisense oligonucleotide to the cell, animal or human in such a way that the antisense compound are able to bind to and modulate the function of its intended target.

As used herein, "hybridisation" means hydrogen bonding, which may be Watson-Crick, Hoogsteen, reversed Hoogsteen hydrogen bonding, etc. between complementary nucleoside or nucleotide bases. Watson and Crick showed approximately fifty years ago that deoxyribo nucleic acid (DNA) is composed of two strands which are held together in a helical configuration by hydrogen bonds formed between opposing complementary nucleobases in the two strands. The four nucleobases, commonly found in DNA are guanine (G), adenine (A), thymine (T) and cytosine (C) of which the G nucleobase pairs with C, and the A nucleobase pairs with T. In RNA the nucleobase thymine is replaced by the nucleobase uracil (U), which similarly to the T nucleobase pairs with A. The chemical groups in the nucleobases that participate in standard duplex formation constitute the Watson-Crick face. Hoogsteen showed a couple of years later that the purine nucleobases (G and A) in addition to their Watson-Crick face have a Hoogsteen face that can be recognised from the outside of a duplex, and used to bind pyrimidine oligonucleotides via hydrogen bonding, thereby forming a triple helix structure.

In the context of the present invention "complementary" refers to the capacity for precise pairing between two nucleotides or nucleoside sequences with one another. For example, if a nucleotide at a certain position of an oligonucleotide is capable of hydrogen bonding with a nucleotide at the corresponding position of a DNA or RNA molecule, then the oligonucleotide and the DNA or RNA are considered to be complementary to each other at that position. The DNA or RNA and the oligonucleotide are considered complementary to each other when a sufficient number of nucleotides in the oligonucleotide can form hydrogen bonds with corresponding nucleotides in the target DNA or RNA to enable the formation of a stable complex. To be stable in vitro or in vivo the sequence of an antisense compound need not be 100% complementary to its target nucleic acid. The terms "complementary" and "specifically hybridisable" thus imply that the antisense compound binds sufficiently strongly and specifically to the target molecule to provide the desired interference with the normal function of the target whilst leaving the function of non-target mRNAs unaffected.

The term "Nucleic Acid Analogues" refers to a non-natural nucleic acid binding compound. Nucleic Acid Analogues are described in e.g. Freier & Altmann (Nucl. Acid Res., 1997, 25, 4429-4443) and Uhlmann (Curr. Opinion in Drug & Development (2000, 3(2): 293-213). Scheme 1 illustrates selected examples.

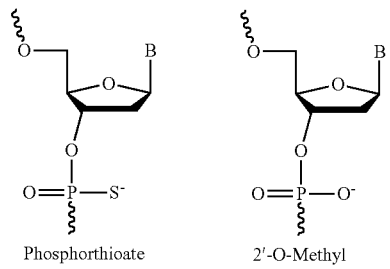

Scheme 1

Phosphorthioate      2'-O-Methyl

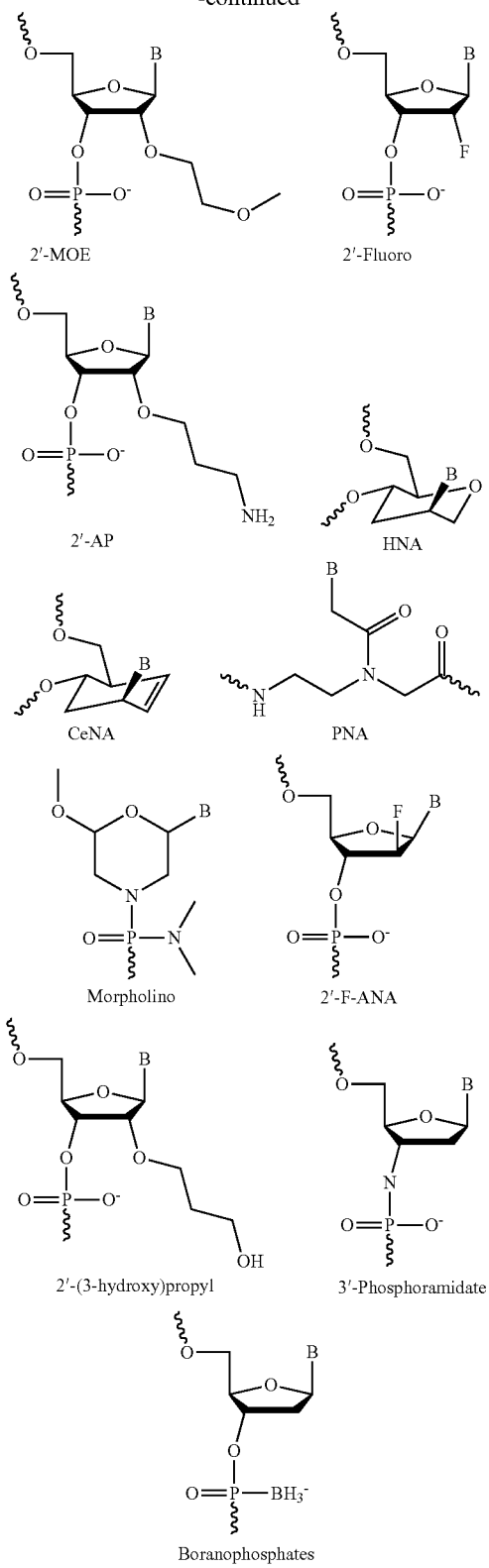

The term "LNA" refers to an oligonucleotide containing one or more bicyclic nucleoside analogues also referred to as a LNA monomer. LNA monomers are described in WO 9914226 and subsequent applications, WO0056746, WO0056748, WO0066604, WO00125248, WO0228875, WO2002094250 and PCT/DK02/00488. One particular example of a thymidine LNA monomer is the (1S,3R,4R,7S)-7-hydroxy-1-hydroxymethyl-5-methyl-3-(thymin-1yl)-2,5-dioxa-bicyclo[2:2:1]heptane.

The term "oligonucleotide" refers, in the context of the present invention, to an oligomer (also called oligo) or nucleic acid polymer (e.g. ribonucleic acid (RNA) or deoxyribonucleic acid (DNA)) or nucleic acid analogue of those known in the art, preferably Locked Nucleic Acid (LNA), or a mixture thereof. This term includes oligonucleotides composed of naturally occurring nucleobases, sugars and internucleoside (backbone) linkages as well as oligonucleotides having non-naturally-occurring portions which function similarly or with specific improved functions. A fully or partly modified or substituted oligonucleotides are often preferred over native forms because of several desirable properties of such oligonucleotides such as for instance, the ability to penetrate a cell membrane, good resistance to extra- and intracellular nucleases, high affinity and specificity for the nucleic acid target. The LNA analogue is particularly preferred exhibiting the above-mentioned properties.

By the term "unit" is understood a monomer.

The term "at least one" comprises the integers larger than or equal to 1, such as 1, 2, 3, 4, 5, 6, 7, 8, 9, 10, 11, 12, 13, 14, 15, 16, 17 and so forth.

The term "thio-LNA" comprises a locked nucleotide in which at least one of X or Y in Scheme 2 is selected from S or —CH$_2$—S—. Thio-LNA can be in both beta-D and alpha-L-configuration.

The term "amino-LNA" comprises a locked nucleotide in which at least one of X or Y in Scheme 2 —N(H)—, N(R)—, CH$_2$—N(H)—, —CH$_2$—N(R)— where R is selected from hydrogen and C$_{1-4}$-alkyl. Amino-LNA can be in both beta-D and alpha-L-configuration.

The term "oxy-LNA" comprises a locked nucleotide in which at least one of X or Y in Scheme 2 represents 0 or —CH$_2$—O—. Oxy-LNA can be in both beta-D and alpha-L-configuration.

The term "ena-LNA" comprises a locked nucleotide in which Y in Scheme 2 is —CH$_2$—O—.

By the term "alpha-L-LNA" comprises a locked nucleotide represented as shown in Scheme 3.

By the term "LNA derivatives" comprises all locked nucleotide in Scheme 2 except beta-D-methylene LNA e.g. thio-LNA, amino-LNA, alpha-L-oxy-LNA and ena-LNA.

DETAILED DESCRIPTION OF THE INVENTION

The present invention employs oligomeric compounds, particularly antisense oligonucleotides, for use in modulating the function of nucleic acid molecules encoding HIF-1α. The modulation is ultimately a change in the amount of HIF-1α produced. In one embodiment this is accomplished by providing antisense compounds, which specifically hybridise with nucleic acids encoding HIF-1α. The modulation is preferably an inhibition of the expression of HIF-1α, which leads to a decrease in the number of functional proteins produced. HIF-1 may be involved in angiogenesis as well as red blood cell proliferation, cellular proliferation, iron metabolism, glucose and energy metabolism, pH regulation, tissue invasion, apoptosis, multi-drug resistance, cellular stress response or matrix metabolism.

Antisense and other oligomeric compounds of the invention, which modulate expression of the target, are identified through experimentation or though rational design based on sequence information on the target and know-how on how best to design an oligomeric compound against a desired target. The sequences of these compounds are preferred embodiments of the invention. Likewise, the sequence motifs in the target to which these preferred oligomeric compounds are complementary (referred to as "hot spots") are preferred sites for targeting.

Figure 3:
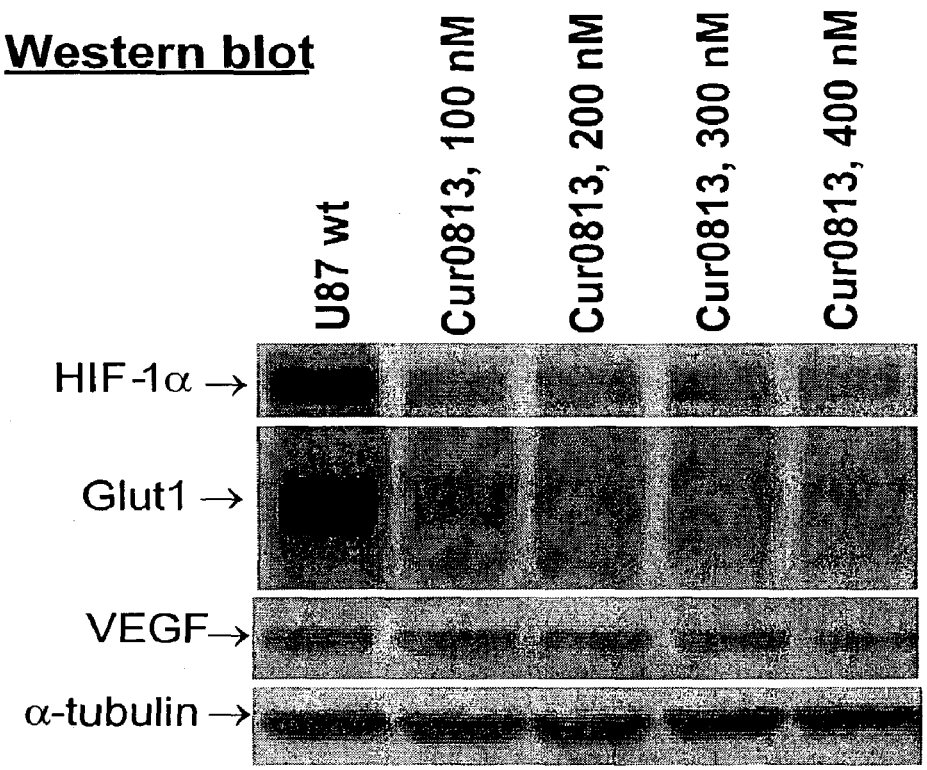
FIG. 3 shows Western blots of HIF-1α, VEGF Glut1 and tubulin protein in U87 cells treated with oligo Cur0813. Cells were treated with oligo for 24 hours at 100 nM, 200 nM, 300 nM and 400 nM. The cells were exposed to severe hypoxia for 18 hours immediately after the treatment.
Figure 3:
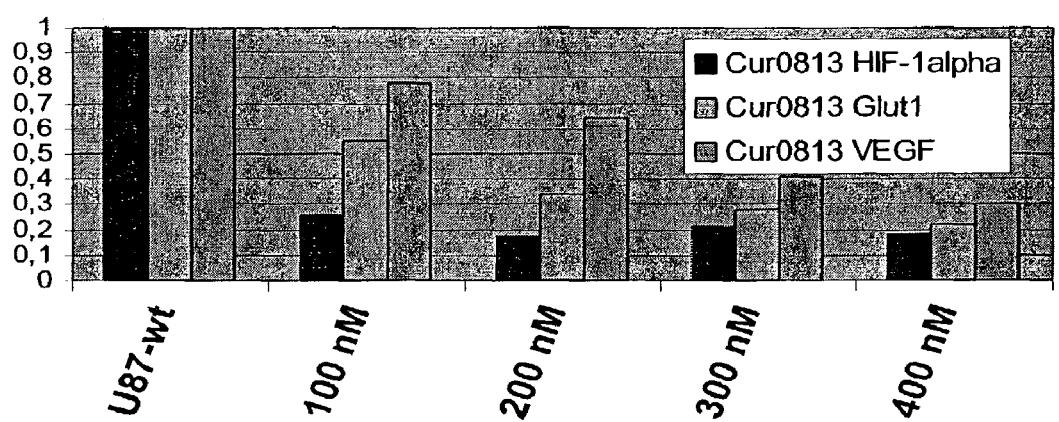
Figure 4:
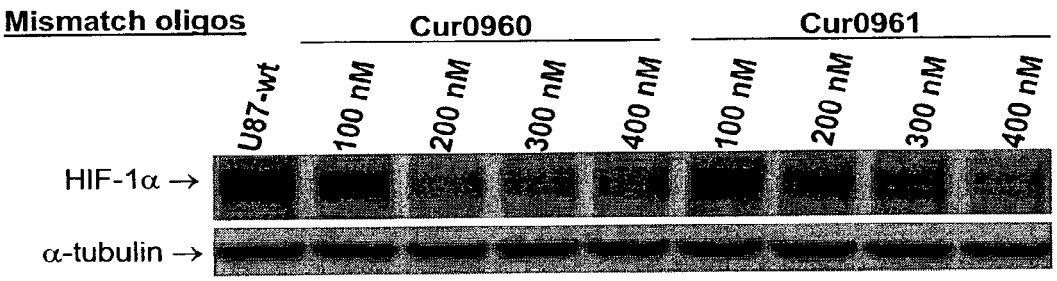
FIG. 4 shows Western blots of HIF-1α and tubulin protein in U87 cells treated with mismatch oligos (Cur0960 and Cur0961). Cells were treated with oligo for 24 hours at 100 nM, 200 nM, 300 nM and 400 nM. The cells were exposed to severe hypoxia for 18 hours immediately after the treatment.
Figure 5:
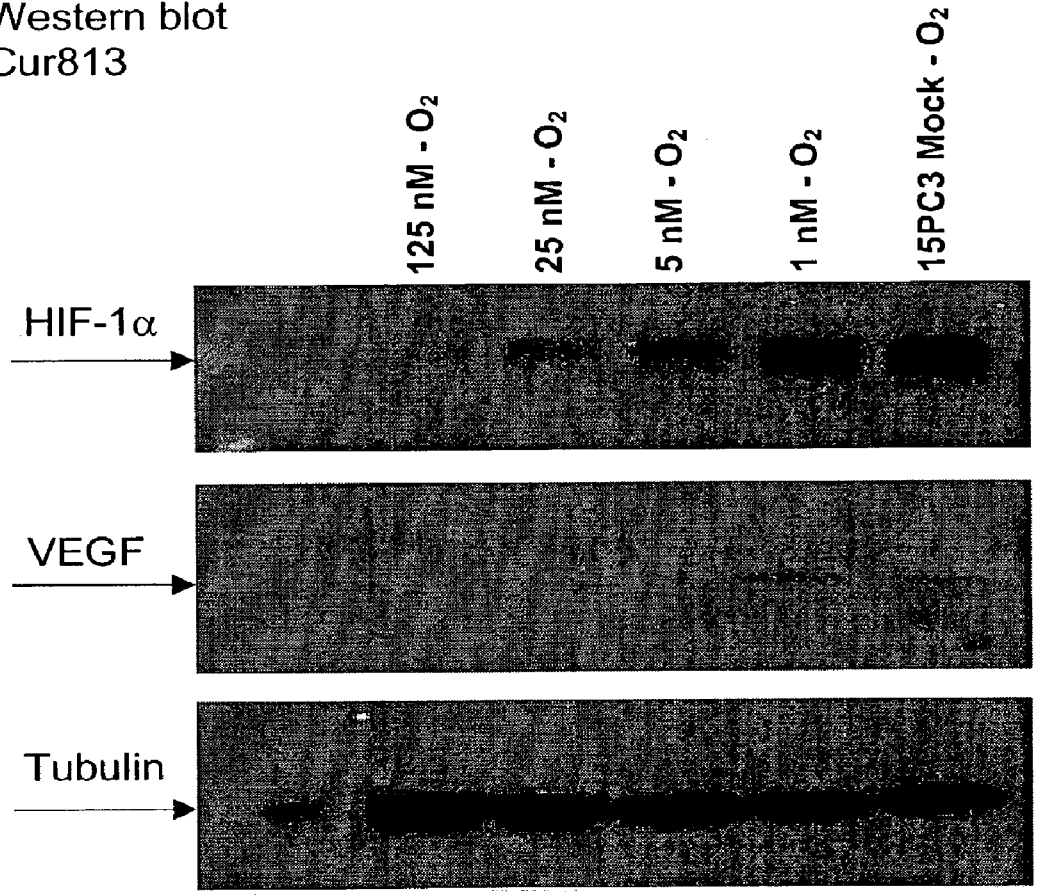
FIG. 5 shows Western blots of HIF-1α, VEGF and tubulin protein in 15PC3 cells treated with oligo Cur813. Cells were treated with oligo for 16 hours at 125 nM, 25 nM, 5 nM and 1 nM. The cells were exposed to severe hypoxia for 6 hours immediately after the treatment.
Figure 6:
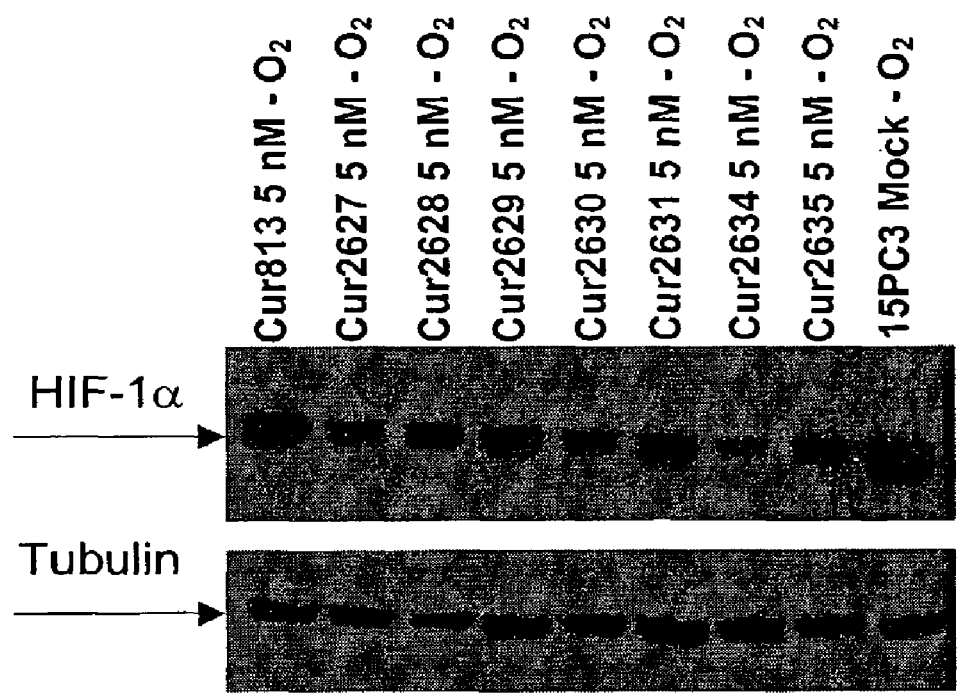
FIG. 6 shows Western blots of HIF-1α and tubulin protein in 15PC3 cells treated with different oligos at 5 nM for 16 hours. The cells were exposed to severe hypoxia for 6 hours immediately after the treatment.
Figure 7:
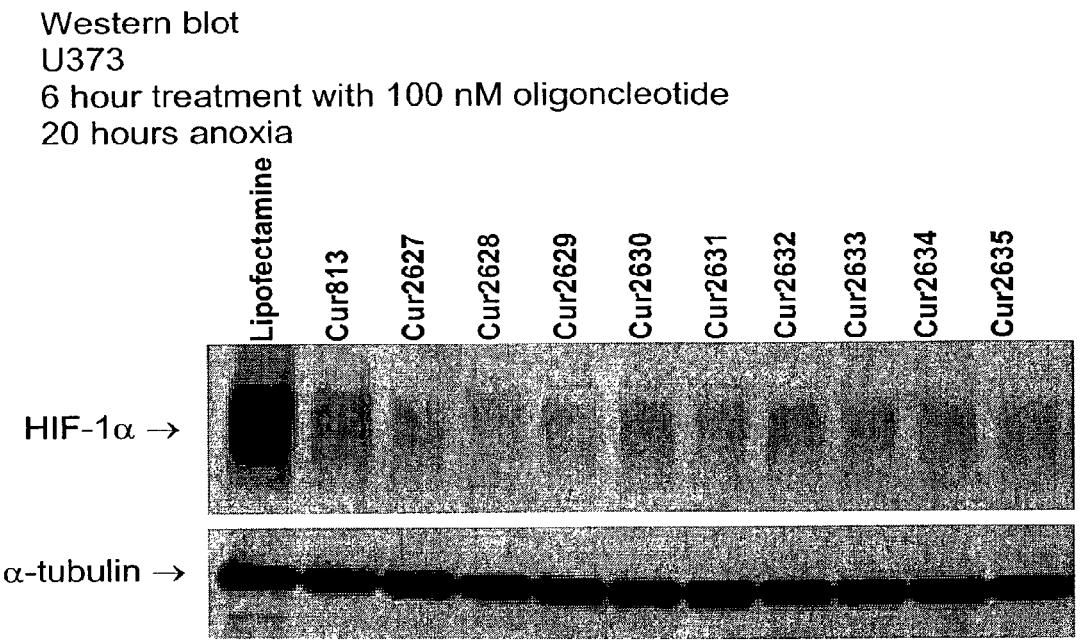
FIG. 7 shows Western blots of HIF-1α and tubulin protein in U373 cells treated with different oligos at 100 nM for 6 hours. The cells were exposed to severe hypoxia for 20 hours immediately after the treatment.
Figure 7:
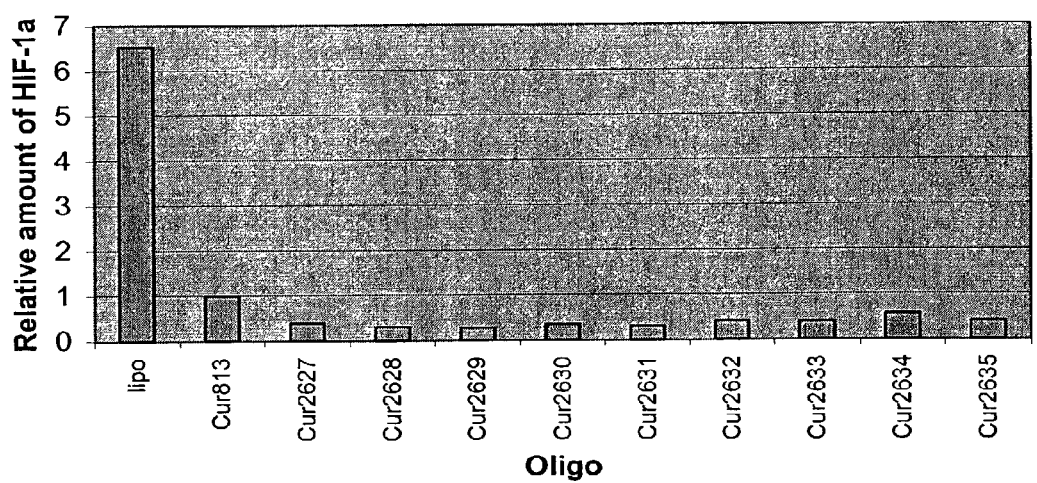
Figure 8:
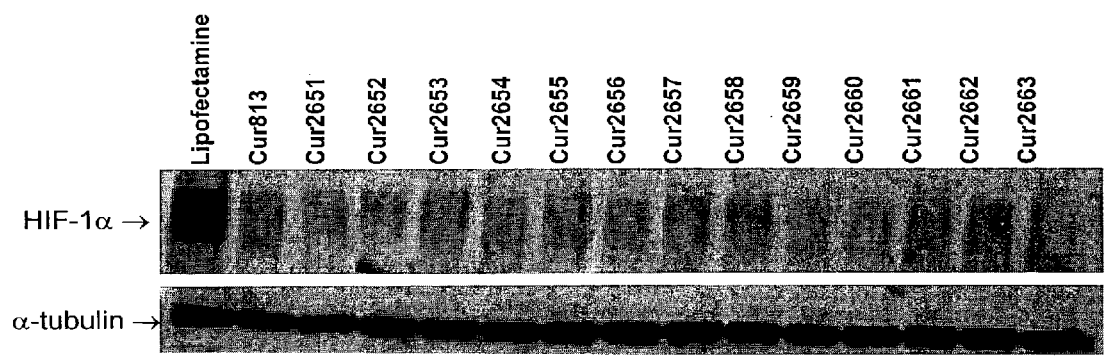
FIG. 8 shows Western blots of HIF-1α and tubulin protein in U373 cells treated with different oligos at 100 nM for 6 hours. The cells were exposed to severe hypoxia for 20 hours immediately after the treatment.
Figure 8:
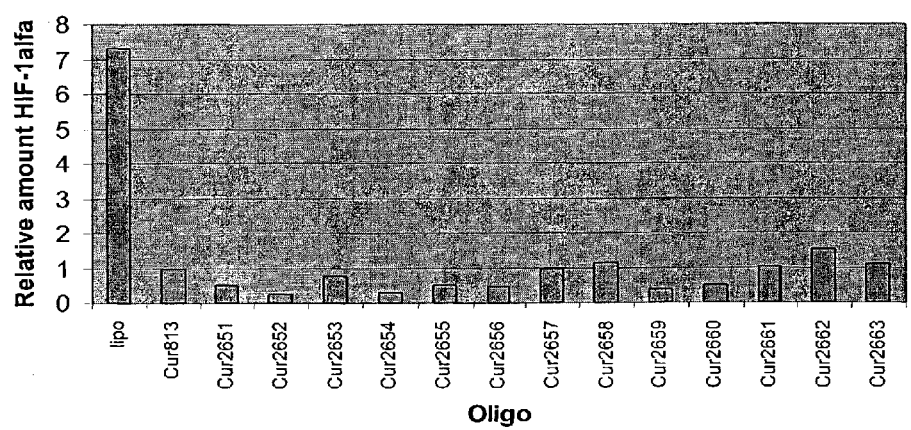
Figure 9:
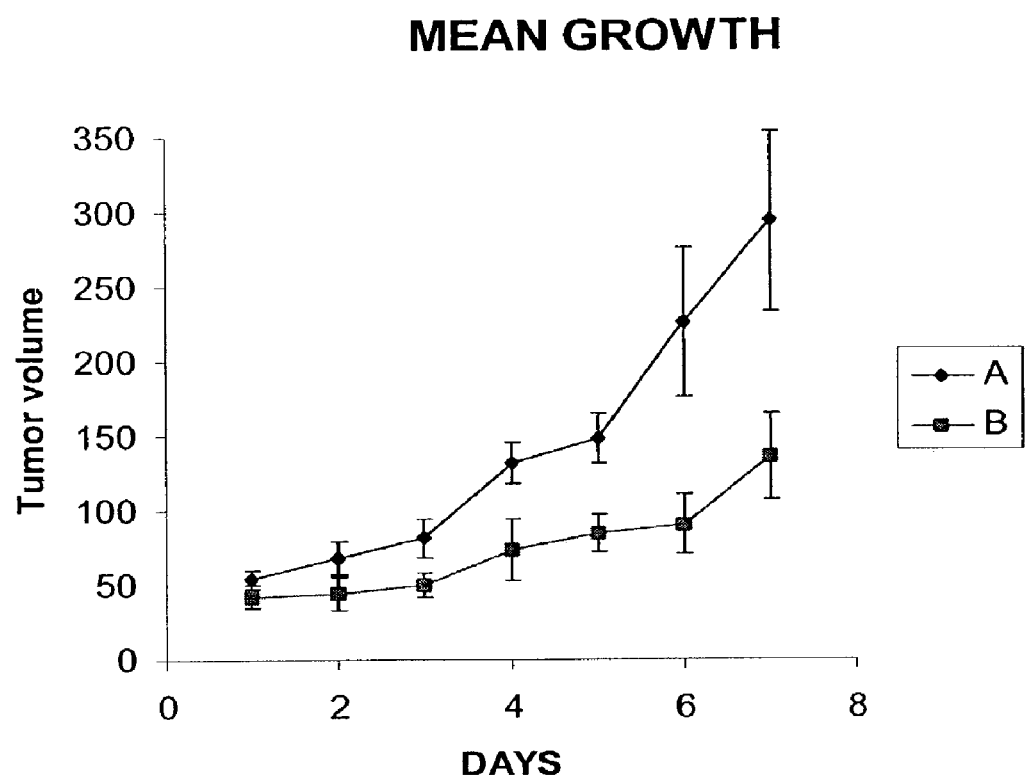
FIG. 9 shows growth curves of U373 xenograft tumours treated with PBS or Cur813 at 5 mg/kg/day i.p. 1× daily for 7 days. Bars represent standard errors.

Preferred oligomeric compounds according to the invention are SEQ ID NO 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114 or 115 and their sequences are presented in table 1 and table 2. The oligomeric compounds according to the invention are potent modulators of target. This is showed experimentally both in vitro and in vivo. In vitro inhibition of target is shown in table 1 and FIGS. 1-8 using three different cancer cell lines. FIG. 9 shows in viva down regulation of target. Furthermore, the oligomeric compounds are shown to be potent inhibitors in much lower concentration than e.g. the standard condition for phosphorthioate antisense oligonucleotides. FIGS. 5 and 6 show inhibition of compounds of the invention down to 5 nM. Inhibition of HIF-1α by oligomeric compounds of the invention can also inhibit the expression of Vascular Endothelial Growth Factor (VEGF) known to be involved in angiogenesis and Glucose Transporter-1 (GLUT-1) known to be involved in glucose uptake as shown in FIGS. 3 and 5. Various designs of oligomeric compounds shown in table 2 targeted to two motifs were identified as potent inhibitors of the target as shown in FIGS. 1 and 7. A genewalk was performed using oligomeric compounds from table 1, and the effect of the potent oligomeric compounds is shown in FIG. 8. All the above-mentioned experimental observations show that the compounds according to the invention can constitute the active compound in a pharmaceutical composition.

Furthermore, the oligomeric compounds according to the invention may inhibit HIF-1α under normoxia and hypoxia.

In one embodiment of the invention the oligomeric compounds are containing at least on unit of chemistry termed LNA (Locked Nucleic Acid).

LNA monomer typically refers to a bicyclic nucleoside analogue, as described in the International Patent Application WO 99/14226 and subsequent applications, WO0056746, WO0056748, WO0066604, WO00125248, WO0228875, WO2002094250 and PCT/DK02/00488 all incorporated herein by reference. Preferred LNA monomers structures are exemplified in Scheme 2

Scheme 2

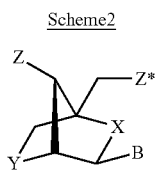

X and Y are independently selected among the groups —O—, —S—, —N(H)—, N(R)—, —CH$_2$— or —CH— (if part of a double bond), —CH$_2$—O—, —CH$_2$—S—, —CH$_2$—N(H)—, —CH$_2$—N(R)—, —CH$_2$—CH$_2$— or —CH$_2$—CH— (if part of a double bond), —CH═CH—, where R is selected from hydrogen and C$_{1-4}$-alkyl. The asymmetric groups may be found in either orientation.

In Scheme 2 the 4 chiral centers are shown in a fixed configuration. However, also comprised in this invention are compounds of the general Scheme 2 in which the chiral centers are found in different configurations. Thus, each chiral center in Scheme 2 can exist in either R or S configuration. The definition of R (rectus) and S (sinister) are described in the IUPAC 1974 Recommendations, Section E, Fundamental Stereochemistry The rules can be found in Pure Appl. Chem. 45, 13-30, (1976) and in "Nomenclature of organic Chemistry" Pergamon, New York, 1979.

Z and Z* are independently selected among an internucleoside linkage, a terminal group or a protecting group.

The internucleoside linkage may be —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$^H$—CO—O—, —NR$^H$—CO—NR$^H$—, —O—CO—O—, —O—CO—NR$^H$—, —NR$^H$—CO—CH$_2$—, —O—CH$_2$—CO—NR$^H$—, —O—CH$_2$—CH$_2$—NR$^H$—, —CO—NR$^H$—CH$_2$—, —CH$_2$—NR$^H$—CO—, —O—CH$_2$—CH$_2$—S—, —S—CH$_2$—CH$_2$—O—, —S—CH$_2$—CH$_2$—S—, —CH$_2$—SO$_2$—CH$_2$—, —CH$_2$—CO—NR$^H$—, —O—CH$_2$—CH$_2$—NR$^H$—CO—, —CH$_2$—NCH$_3$—O—CH$_2$—, where R$^H$ is selected form hydrogen and C$_{1-4}$-alkyl, The terminal groups are selected independently from hydrogen, azido, halogen, cyano, nitro, hydroxy, Prot-O—, Act-O—, mercapto, Prot-S—, Act-S—, C$_{1-6}$-alkylthio, amino, Prot-N(R$^H$)—, Act-N(R$^H$)—, mono- or di(C$_{1-6}$-alkyl)amino, optionally substituted C$_{1-6}$-alkoxy, optionally substituted C$_{1-6}$-alkyl, optionally substituted C$_{2-6}$-alkenyl, optionally substituted C$_{2-6}$-alkenyloxy, optionally substituted C$_{2-6}$-alkynyl, optionally substituted C$_{2-6}$-alkynyloxy, monophosphate—or protected monophosphate, monothiophosphate—or protected monothiophosphate, diphosphate—or protected diphosphate, dithiophosphate—or protected dithiophosphate, triphosphate—or protected triphosphate, trithiophosphate—or protected trithiophosphate. Examples of such protection groups on the phosphate residues are S-acetylthioethyl (SATE) or S-pivaloylthioethyl (t-butyl-SATE), DNA intercalators, photochemically active groups, thermochemically active groups, chelating groups, reporter groups, ligands, carboxy, sulphono, hydroxymethyl, Prot—O—CH$_2$—, Act—O—CH$_2$—, aminomethyl, Prot-N(R$^H$)—CH$_2$-Act-N(R$^H$)—CH$_2$—, carboxymethyl, sulphonomethyl, where Prot is a protection group for —OH, —SH, and —NH(R$^H$), respectively, Act is an activation group for —OH, —SH, and —NH(R$^H$), respectively, and R$^H$ is selected from hydrogen and C$_{1-6}$-alkyl;

The protection groups of hydroxy substituents comprises substituted trityl, such as 4,4'-dimethoxytrityloxy (DMT), 4-monomethoxytrityloxy (MMT), and trityloxy, optionally substituted 9-(9-phenyl)xanthenyloxy (pixyl), optionally substituted methoxytetrahydropyranyloxy (mthp), silyloxy such as trimethylsilyloxy (TMS), triisopropylsilyloxy (TIPS), tert-butyldimethylsilyloxy (TBDMS), triethylsilyloxy, and phenyldimethylsilyloxy, tert-butylethers, acetals (including two hydroxy groups), acyloxy such as acetyl or halogen substituted acetyls, e.g. chloroacetyloxy or fluoroacetyloxy, isobutyryloxy, pivaloyloxy, benzoyloxy and substituted benzoyls, methoxymethyloxy (MOM), benzyl ethers or substituted benzyl ethers such as 2,6-dichlorobenzyloxy (2,6-CL$_2$Bz1). Alternatively when Z or Z* is hydroxyl they may be protected by attachment to a solid support optionally through a linker.

When Z or Z* is amino groups illustrative examples of the amino protection protections are fluorenylmethoxycarbonylamino (Fmoc), tert-butyloxycarbonylamino (BOC), trifluoroacetylamino, allyloxycarbonylamino (alloc, AOC), Z benzyl-oxycarbonylamino (Cbz), substituted benzyloxycarbonylaminos such as 2-chloro benzyloxycarbonylamino (2-ClZ), monomethoxytritylamino (MMT), dimethoxytritylamino (DMT), phthaloylamino, and 9-(9-phenyl)xanthenylamino (pixyl).

In the embodiment above, Act designates an activation group for —OH, —SH, and —NH($R^H$). In a preferred embodiment such activators mediates couplings to other residues, monomers. After such successful couplings the act-group is converted to an internucleoside linkage. Such activation groups are, e.g., selected from optionally substituted O-phosphoramidite, optionally substituted O-phosphortriester, optionally substituted O-phosphordiester, optionally substituted H-phosphonate, and optionally substituted O-phosphonate.

In the present context, the term "phosphoramidite" means a group of the formula —P($OR^x$)—N($R^y$)$_2$, wherein $R^x$ designates an optionally substituted alkyl group, e.g. methyl, 2-cyanoethyl, or benzyl, and each of $R^y$ designate optionally substituted alkyl groups, e.g. ethyl or isopropyl, or the group —N($R^y$)$_2$ forms a morpholino group (—N(CH$_2$CH$_2$)$_2$O). $R^x$ preferably designates 2-cyanoethyl and the two $R^y$ are preferably identical and designate isopropyl. Thus, an especially relevant phosphoramidite is N,N-diisopropyl-O-(2-cyanoethyl)phosphoramidite.

B constitutes a natural or non-natural nucleobase and selected among adenine, cytosine, 5-methylcytosine, isocytosine, pseudoisocytosine, guanine, thymine, uracil, 5-bromouracil, 5-propynyluracil, 5-propyny-6-fluoroluracil, 5-methylthiazoleuracil, 6-aminopurine, 2-aminopurine, inosine, diaminopurine, 7-propyne-7-deazaadenine, 7-propyne-7-deazaguanine, 2-chloro-6-aminopurine.

Particularly preferred bicyclic structures are shown in Scheme 3 below:

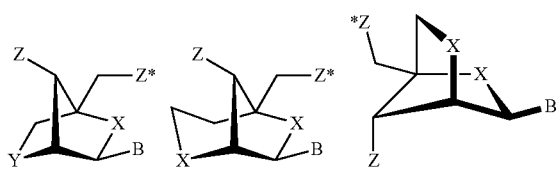

Scheme 3 when at least one X=O

Where X is —O—, —S—, —NH—, and N($R^H$),
Z and Z* are independently selected among an internucleoside linkage, a terminal group or a protecting group.

The internucleotide linkage may be —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO($R^H$)—O—, O—PO(OCH$_3$)—O—, —O—PO(N$R^H$)—O—, —O—PO(OCH$_2$CH$_2$S—R)—O—, —O—PO(BH$_3$)—O—, —O—PO(NH$R^H$)—O—, —O—P(O)$_2$—N$R^H$—, —N$R^H$—P(O)$_2$—O—, —N$R^H$—CO—O—, where $R^H$ is selected form hydrogen and C$_{1-4}$-alkyl.

The terminal groups are selected independently among from hydrogen, azido, halogen, cyano, nitro, hydroxy, Prot-O—, Act-O—, mercapto, Prot-S—, Act-S—, C$_{1-6}$-alkylthio, amino, Prot-N($R^H$)—, Act-N($R^H$)—, mono- or di(C$_{1-6}$-alkyl)amino, optionally substituted C$_{1-6}$-alkoxy, optionally substituted C$_{1-6}$-alkyl, optionally substituted monophosphate, monothiophosphate, diphosphate, dithiophosphate triphosphate, trithiophosphate, where Prot is a protection group for —OH, —SH, and —NH($R^H$), respectively, Act is an activation group for —OH, —SH, and —NH(O), respectively, and $R^H$ is selected from hydrogen and C$_{1-6}$-alkyl.

The protection groups of hydroxy substituents comprises substituted trityl, such as 4,4'-dimethoxytrityloxy (DMT), 4-monomethoxytrityloxy (MMT), optionally substituted 9-(9-phenyl)xanthenyloxy (pixyl), optionally substituted methoxytetra-hydropyranyloxy (mthp), silyloxy such as trimethylsilyloxy (TMS), triisopropylsilyloxy (TIPS), tert-butyldimethylsilyloxy (TBDMS), triethylsilyloxy, and phenyldimethylsilyloxy, tert-butylethers, acetals (including two hydroxy groups), acyloxy such as acetyl Alternatively when Z or Z* is hydroxyl they may be protected by attachment to a solid support optionally through a linker.

When Z or Z* is amino groups illustrative examples of the amino protection protections are fluorenylmethoxycarbonylamino (Fmoc), tert-butyloxycarbonylamino (BOC), trifluoroacetylamino, allyloxycarbonylamino (alloc, AOC), monomethoxytritylamino (MMT), dimethoxytritylamino (DMT), phthaloylamino.

In the embodiment above, Act designates an activation group for —OH, —SH, and —NH($R^H$). In a preferred embodiment such activators mediates couplings to other residues, monomers. After such successful couplings the act-group is converted to an internucleoside linkage. Such activation groups are, e.g., selected from optionally substituted O-phosphoramidite, optionally substituted O-phosphortriester, optionally substituted O-phosphordiester, optionally substituted H-phosphonate, and optionally substituted O-phosphonate.

In the present context, the term "phosphoramidite" means a group of the formula —P($OR^x$)—N($R^y$)$_2$, wherein $R^x$ designates an optionally substituted alkyl group, e.g. methyl, 2-cyanoethyl, and each of $R^y$ designate optionally substituted alkyl groups, $R^x$ preferably designates 2-cyanoethyl and the two $R^y$ are preferably identical and designate isopropyl. Thus, an especially relevant phosphoramidite is N,N-diisopropyl-O-(2-cyanoethyl)phosphoramidite.

B constitutes a natural or non-natural nucleobase and selected among adenine, cytosine, 5-methylcytosine, isocytosine, pseudoisocytosine, guanine, thymine, uracil, 5-bromouracil, 5-propynyluracil, 6-aminopurine, 2-aminopurine, inosine, diaminopurine, 2-chloro-6-aminopurine.

Therapeutic Principle

A person skilled in the art will appreciate that oligomeric compounds containing LNA can be used to combat HIF-1α linked diseases by many different principles, which thus falls within the spirit of the present invention.

For instance, LNA oligomeric compounds may be designed as antisense inhibitors, which are single stranded nucleic acids that prevent the production of a disease causing protein, by intervention at the mRNA level. Also, they may be designed as Ribozymes or Oligozymes which are antisense oligonucleotides which in addition to the target binding domain(s) comprise a catalytic activity that degrades the target mRNA (ribozymes) or comprise an external guide sequence (EGS) that recruit an endogenous enzyme (RNase P) which degrades the target mRNA (oligozymes)

Equally well, the LNA oligomeric compounds may be designed as siRNA's which are small double stranded RNA molecules that are used by cells to silence specific endogenous or exogenous genes by an as yet poorly understood "antisense-like" mechanism.

LNA oligomeric compounds may also be designed as Aptamers (and a variation thereof, termed Spiegelmers) which are nucleic acids that through intra-molecular hydrogen bonding adopt three-dimensional structures that enable them to bind to and block their biological targets with high affinity and specificity. Also, LNA oligomeric compounds may be designed as Decoys, which are small double-stranded nucleic acids that prevent cellular transcription factors from transactivating their target genes by selectively blocking their DNA binding site.

Furthermore, LNA oligomeric compounds may be designed as Chimeraplasts, which are small single stranded nucleic acids that are able to specifically pair with and alter a target gene sequence. LNA containing oligomeric compounds exploiting this principle therefore may be particularly useful for treating HIF-1α linked diseases that are caused by a mutation in the HIF-1α gene.

Finally, LNA oligomeric compounds may be designed as TFO's (triplex forming oligonucleotides), which are nucleic acids that bind to double stranded DNA and prevent the production of a disease causing protein, by intervention at the RNA transcription level.

Dictated in part by the therapeutic principle by which the oligonucleotide is intended to operate, the LNA oligomeric compounds in accordance with this invention preferably comprise from about 8 to about 60 nucleobases i.e. from about 8 to about 60 linked nucleosides. Particularly preferred compounds are antisense oligonucleotides comprising from about 12 to about 30 nucleobases and most preferably are antisense compounds comprising about 12-20 nucleobases.

Referring to the above principles by which an LNA oligomeric compound can elicit its therapeutic action the target of the present invention may be the HIF-1α gene, the mRNA or the protein. In the most preferred embodiment the LNA oligomeric compounds is designed as an antisense inhibitor directed against the HIF-1α a pre-mRNA or HIF-1α mRNA. The oligonucleotides may hybridize to any site along the HIF-1α pre-mRNA or mRNA such as sites in the 5' untranslated leader, exons, introns and 3' untranslated tail.

In a preferred embodiment, the oligonucleotide hybridizes to a portion of the human HIF-1α pre-mRNA or mRNA that comprises the translation-initiation site. More preferably, the HIF-1α oligonucleotide comprises a CAT sequence, which is complementary to the AUG initiation sequence of the HIF-1α pre-mRNA or RNA. In another embodiment, the HIF-1α oligonucleotide hybridizes to a portion of the splice donor site of the human HIF-1α pre-mRNA. In yet another embodiment, HIF-1αoligonucleotide hybridizes to a portion of the splice acceptor site of the human HIF-1α a pre-mRNA. In another embodiment, the HIF-1α oligonucleotide hybridizes to portions of the human HIF-1α pre-mRNA or mRNA involved in polyadenylation, transport or degradation.

The skilled person will appreciate that preferred oligonucleotides are those that hybridize to a portion of the HIF-1α pre-mRNA or mRNA whose sequence does not commonly occur in transcripts from unrelated genes so as to maintain treatment specificity.

The oligomeric compound of the invention are designed to be sufficiently complementary to the target to provide the desired clinical response e.g. the oligomeric compound must bind with sufficient strength and specificity to its target to give the desired effect. In one embodiment, said compound modulating HIF-1α is designed so as to also modulate other specific nucleic acids which do not encode HIF-1α.

It is preferred that the oligomeric compound according to the invention is designed so that intra- and intermolecular oligonucleotide hybridisation is avoided.

In many cases the identification of an LNA oligomeric compound effective in modulating HIF-1α activity in vivo or clinically is based on sequence information on the target gene. However, one of ordinary skill in the art will appreciate that such oligomeric compounds can also be identified by empirical testing. As such HIF-1α oligomeric compounds having, for example, less sequence homology, greater or fewer modified nucleotides, or longer or shorter lengths, compared to those of the preferred embodiments, but which nevertheless demonstrate responses in clinical treatments, are also within the scope of the invention.

Antisense Drugs

In one embodiment of the invention the oligomeric compounds are suitable antisense drugs. The design of a potent and safe antisense drug requires the fine-tuning of diverse parameters such as affinity/specificity, stability in biological fluids, cellular uptake, mode of action, pharmacokinetic properties and toxicity.

Affinity & specificity: LNA with an oxymethylene 2'-O, 4'-C linkage (β-D-oxy-LNA), exhibits unprecedented binding properties towards DNA and RNA target sequences. Likewise LNA derivatives, such as amino-, thio- and α-L-oxy-LNA display unprecedented affinities towards complementary RNA and DNA and in the case of thio-LNA the affinity towards RNA is even better than with the β-D-oxy-LNA.

In addition to these remarkable hybridization properties, LNA monomers can be mixed and act cooperatively with DNA and RNA monomers, and with other nucleic acid analogues, such as 2'-O-alkyl modified RNA monomers. As such, the oligonucleotides of the present invention can be composed entirely of β-D-oxy-LNA monomers or it may be composed of β-D-oxy-LNA in any combination with DNA, RNA or contemporary nucleic acid analogues which includes LNA derivatives such as for instance amino-, thio- and α-L-oxy-LNA. The unprecedented binding affinity of LNA towards DNA or RNA target sequences and its ability to mix freely with DNA, RNA and a range of contemporary nucleic acid analogues has a range of important consequences according to the invention for the development of effective and safe antisense compounds.

Firstly, in one embodiment of the invention it enables a considerable shortening of the usual length of an antisense oligo (from 20-25 mers to, e.g., 12-15 mers) without compromising the affinity required for pharmacological activity. As the intrinsic specificity of an oligo is inversely correlated to its length, such a shortening will significantly increase the specificity of the antisense compound towards its RNA target. One embodiment of the invention is to, due to the sequence of the human genome is available and the annotation of its genes rapidly progressing, identify the shortest possible, unique sequences in the target mRNA.

In another embodiment, the use of LNA to reduce the size of oligos significantly eases the process and prize of manufacture thus providing the basis for antisense therapy to become a commercially competitive treatment offer for a diversity of diseases.

In another embodiment, the unprecedented affinity of LNA can be used to substantially enhance the ability of an antisense oligo to hybridize to its target mRNA in-vivo thus significantly reducing the time and effort required for identifying an active compound as compared to the situation with other chemistries.

In another embodiment, the unprecedented affinity of LNA is used to enhance the potency of antisense oligonucleotides thus enabling the development of compounds with more favorable therapeutic windows than those currently in clinical trials.

When designed as an antisense inhibitor, the oligonucleotides of the invention bind to the target nucleic acid and modulate the expression of its cognate protein. Preferably, such modulation produces an inhibition of expression of at least 10% or 20% compared to the normal expression level, more preferably at least a 30%, 40%, 50%, 60%, 70%, 80%, or 90% inhibition compared to the normal expression level.

Typically, the LNA oligonucleotides of the invention will contain other residues than 13-D-oxy-LNA such as native DNA monomers, RNA monomers, N3'-P5'phosphoroamidates, 2'-F, 2'-O-Me, 2'-O-methoxyethyl (MOE), 2'-O-(3-aminopropyl) (AP), hexitol nucleic acid (HNA), 2'-F-arabino nucleic acid (2'-F-ANA) and D-cyclohexenyl nucleoside (CeNA). Also, the β-D-oxy-LNA-modified oligonucleotide may also contain other LNA units in addition to or in place of an oxy-LNA group. In particular, preferred additional LNA units include thio-LNA or amino-LNA monomers in either the D-β or L-α configurations or combinations thereof or ena-LNA. In general, an LNA-modified oligonucleotide will contain at least about 5, 10, 15 or 20 percent LNA units, based on total nucleotides of the oligonucleotide, more typically at least about 20, 25, 30, 40, 50, 60, 70, 80 or 90 percent LNA units, based on total bases of the oligonucleotide.

Stability in biological fluids: One embodiment of the invention includes the incorporation of LNA monomers into a standard DNA or RNA oligonucleotide to increase the stability of the resulting oligomeric compound in biological fluids e.g. through the increase of resistance towards nucleases (endonucleases and exonucleases). The extent of stability will depend on the number of LNA monomers used, their position in the oligonucleotide and the type of LNA monomer used. Compared to DNA and phosphorothioates the following order of ability to stabilize an oligonucleotide against nucleolytic degradation can be established: DNA<<phosphorothioates~oxy-LNA<α-L-LNA<amino-LNA<thio-LNA.

Given the fact that LNA is compatible with standard DNA synthesis and mixes freely with many contemporary nucleic acid analogues nuclease resistance of LNA-oligomeric compounds can be further enhanced according to the invention by either incorporating other analogues that display increased nuclease stability or by exploiting nuclease-resistant internucleoside linkages e.g. phosphoromonothioate, phosphorodithioate, and methylphosphonate linkages, etc.

Mode of action: Antisense compounds according to the invention may elicit their therapeutic action via a variety of mechanisms and may be able to combine several of these in the same compound. In one scenario, binding of the oligonucleotide to its target (pre-mRNA or mRNA) acts to prevent binding of other factors (proteins, other nucleic acids, etc.) needed for the proper function of the target i.e. operate by steric hindrance. For instance, the antisense oligonucleotide may bind to sequence motifs in either the pre-mRNA or mRNA that are important for recognition and binding of transacting factors involved in splicing, poly-adenylation, cellular transport, post-transcriptional modifications of nucleosides in the RNA, capping of the 5'-end, translation, etc. In the case of pre-mRNA splicing, the outcome of the interaction between the oligonucleotide and its target may be either suppression of expression of an undesired protein, generation of alternative spliced mRNA encoding a desired protein or both. In another embodiment, binding of the oligonucleotide to its target disables the translation process by creating a physical block to the ribosomal machinery, i.e. tranlational arrest.

In yet another embodiment, binding of the oligonucleotide to its target interferes with the RNAs ability to adopt secondary and higher order structures that are important for its proper function, i.e. structural interference. For instance, the oligonucleotide may interfere with the formation of stem-loop structures that play crucial roles in different functions, such as providing additional stability to the RNA or adopting essential recognition motifs for different proteins.

In still another embodiment, binding of the oligonucleotide inactivates the target toward further cellular metabolic processes by recruiting cellular enzymes that degrades the mRNA. For instance, the oligonucleotide may comprise a segment of nucleosides that have the ability to recruit ribonuclease H (RNaseH) that degrades the RNA part of a DNA/RNA duplex. Likewise, the oligonucleotide may comprise a segment which recruits double stranded RNAses, such as for instance RNAseIII or it may comprise an external guide sequence (EGS) that recruit an endogenous enzyme (RNase P) which degrades the target mRNA. Also, the oligonucleotide may comprise a sequence motif which exhibit RNAse catalytic activity or moieties may be attached to the oligonucleotides which when brought into proximity with the target by the hybridization event disables the target from further metabolic activities.

It has been shown that β-D-oxy-LNA does not support RNaseH activity. However, this can be changed according to the invention by creating chimeric oligonucleotides composed of β-D-oxy-LNA and DNA, called gapmers. A gapmer is based on a central stretch of 4-12 nt DNA or modified monomers recognizable and cleavable by the RNaseH (the gap) typically flanked by 1 to 6 residues of β-D-oxy-LNA (the flanks). The flanks can also be constructed with LNA derivatives. There are other chimeric constructs according to the invention that are able to act via an RNaseH mediated mechanism. A headmer is defined by a contiguous stretch of β-D-oxy-LNA or LNA derivatives at the 5'-end followed by a contiguous stretch of DNA or modified monomers recognizable and cleavable by the RNaseH towards the 3'-end, and a tailmer is defined by a contiguous stretch of DNA or modified monomers recognizable and cleavable by the RNaseH at the 5'-end followed by a contiguous stretch of β-D-oxy-LNA or LNA derivatives towards the 3'-end. Other chimeras according to the invention, called mixmers consisting of an alternate composition of DNA or modified monomers recognizable and cleavable by RNaseH and β-D-oxy-LNA and/or LNA derivatives might also be able to mediate RNaseH binding and cleavage. Since α-L-LNA recruits RNaseH activity to a certain extent, smaller gaps of DNA or modified monomers recognizable and cleavable by the RNaseH for the gapmer construct might be required, and more flexibility in the mixmer construction might be introduced. FIG. 1 shows an outline of different designs according to the invention.

Pharmacokinetic Properties

The clinical effectiveness of antisense oligonucleotides depends to a significant extent on their pharmacokinetics e.g. absorption, distribution, cellular uptake, metabolism and excretion. In turn these parameters are guided significantly by the underlying chemistry and the size and three-dimensional structure of the oligonucleotide.

As mentioned earlier LNA according to the invention is not a single, but several related chemistries, which although molecularly different all exhibit stunning affinity towards complementary DNA and RNA, Thus, the LNA family of chemistries are uniquely suited of development oligos according to the invention with tailored pharmacokinetic properties exploiting either the high affinity of LNA to modulate the size of the active compounds or exploiting different LNA chemistries to modulate the exact molecular composition of the active compounds. In the latter case, the use of for instance amino-LNA rather than oxy-LNA will change the overall charge of the oligo and affect uptake and distribution behavior. Likewise the use of thio-LNA instead of oxy-LNA will increase the lipophilicity of the oligonucleotide and thus influence its ability to pass through lipophilic barriers such as for instance the cell membrane.

Modulating the pharmacokinetic properties of an LNA oligonucleotide according to the invention may further be achieved through attachment of a variety of different moieties. For instance, the ability of oligonucleotides to pass the cell membrane may be enhanced by attaching for instance lipid moieties such as a cholesterol moiety, a thioether, an aliphatic chain, a phospholipid or a polyamine to the oligonucleotide. Likewise, uptake of LNA oligonucleotides into cells may be enhanced by conjugating moieties to the oligonucleotide that interacts with molecules in the membrane, which mediates transport into the cytoplasm.

Pharmacodynamic Properties

The pharmacodynamic properties can according to the invention be enhanced with groups that improve oligomer uptake, enhance biostability such as enhanced oligomer resistance to degradation, and/or increase the specificity and affinity of oligonucleotides hybridisation characteristics with target sequence e.g. a mRNA sequence.

Toxicology

There are basically two types of toxicity associated with antisense oligos: sequence-dependant toxicity, involving the base sequence, and sequence-independent, class-related toxicity. With the exception of the issues related to immunostimulation by native CpG sequence motifs, the toxicities that have been the most prominent in the development of antisense oligonucleotides are independent of the sequence, e.g. related to the chemistry of the oligonucleotide and dose, mode, frequency and duration of administration. The phosphorothioates class of oligonucleotides have been particularly well characterized and found to elicit a number of adverse effects such as complement activation, prolonged PTT (partial thromboplastin time), thrombocytopenia, hepatotoxicity (elevation of liver enzymes), cardiotoxicity, splenomegaly and hyperplasia of reticuloendothelial cells.

As mentioned earlier, the LNA family of chemistries provide unprecedented affinity, very high bio-stability and the ability to modulate the exact molecular composition of the oligonucleotide. In one embodiment of the invention, LNA containing compounds enables the development of oligonucleotides which combine high potency with little—if any—phosphorothioate linkages and which are therefore likely to display better efficacy and safety than contemporary antisense compounds.

Manufacture

Oligo- and polynucleotides of the invention may be produced using the polymerisation techniques of nucleic acid chemistry well known to a person of ordinary skill in the art of organic chemistry. Generally, standard oligomerisation cycles of the phosphoramidite approach (S. L. Beaucage and R. P. Iyer, Tetrahedron, 1993, 49, 6123; S. L. Beaucage and R. P. Iyer, Tetrahedron, 1992, 48, 2223) is used, but e.g. H-phosphonate chemistry, phosphortriester chemistry can also be used.

For some monomers of the invention longer coupling time, and/or repeated couplings with fresh reagents, and/or use of more concentrated coupling reagents were used.

The phosphoramidites employed coupled with satisfactory>98% step-wise coupling yields. Thiolation of the phosphate is performed by exchanging the normal, e.g. iodine/pyridine/$H_2O$, oxidation used for synthesis of phosphordiester oligomers with an oxidation using Beaucage's reagent (commercially available) other sulfurisation reagents are also comprised. The phosphorthioate LNA oligomers were efficiently synthesised with stepwise coupling yields>=98%.

The β-D-amino-LNA, β-D-thio-LNA oligonucleotides, α-L-LNA and β-D-methylamino-LNA oligonucleotides were also efficiently synthesised with step-wise coupling yields≧98% using the phosphoramidite procedures.

Purification of LNA oligomeric compounds was done using disposable reversed phase purification cartridges and/or reversed phase HPLC and/or precipitation from ethanol or butanol. Gel electrophoresis, reversed phase HPLC, MALDI-MS, and ESI-MS was used to verify the purity of the synthesized oligonucleotides. Furthermore, solid support materials having immobilised thereto an optionally nucleobase protected and optionally 5'-OH protected LNA are especially interesting as material for the synthesis of LNA containing oligomeric compounds where an LNA monomer is included in at the 3' end. In this instance, the solid support material is preferable CPG, e.g. a readily (commercially) available CPG material or polystyrene onto which a 3'-functionalised, optionally nucleobase protected and optionally 5'-OH protected LNA is linked using the conditions stated by the supplier for that particular material.

Indications

The pharmaceutical composition according to the invention can be used for the treatment of many different diseases. For example HIF-1α has been found to be overexpressed in various solid human tumours and their metastases, e.g. tumours of the breast, colon, prostate, pancreas, brain, lung, ovary, gastro-intestinal system, head and neck, liver, bladder and cervix (Zhong, H. et al., Cancer Research 59, 5830-5835, 1999; Talks, K. L. et al., American Journal of Pathology 157(2), 411-421, 2000)

The methods of the invention is preferably employed for treatment or prophylaxis against diseases caused by cancer, particularly for treatment of cancer as may occur in tissue such as lung, breast, colon, prostate, pancreas, liver, brain, testes, stomach, intestine, bowel, spinal cord, sinuses, cervix, urinary tract or ovaries cancer.

Furthermore, the invention described herein encompasses a method of preventing or treating cancer comprising a therapeutically effective amount of a HIF-1α modulating oligomeric compound, including but not limited to high doses of the oligomer, to a human in need of such therapy. The invention further encompasses the use of a short period of administration of a HIF-1α modulating oligomeric compound. Normal, non-cancerous cells divide at a frequency characteristic for the particular cell type. When a cell has been transformed into a cancerous state, uncontrolled cell proliferation and reduced cell death results, and therefore, promiscuous cell division or cell growth is a hallmark of a cancerous cell type. Examples of types of cancer, include, but are not limited to, non-Hodgkin's lymphoma, Hodgkin's lymphoma, leukemia (e.g., acute leukemia such as acute lymphocytic leukemia, acute myelocytic leukemia, chronic myeloid leukemia, chronic lymphocytic leukemia, multiple myeloma), colon carcinoma, rectal carcinoma, pancreatic cancer, breast cancer, ovarian cancer, prostate cancer, renal cell carcinoma, hepatoma, bile duct carcinoma, choriocarcinoma, cervical cancer, testicular cancer, lung carcinoma, bladder carcinoma, melanoma, head and neck cancer, brain cancer, cancers of unknown primary site, neoplasms, cancers of the peripheral nervous system, cancers of the central nervous system, tumors (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, seminoma, embryonal carcinoma, Wilms' tumor, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, and retinoblastoma), heavy chain disease, metastases, or any disease or disorder characterized by uncontrolled or abnormal cell growth.

Pharmaceutical Composition

It should be understood that the invention also relates to a pharmaceutical composition, which comprises a least one antisense oligonucleotide construct of the invention as an active ingredient. It should be understood that the pharmaceutical composition according to the invention optionally comprises a pharmaceutical carrier, and that the pharmaceutical composition optionally comprises further antisense compounds, chemotherapeutic compounds, anti-inflammatory compounds, antiviral compounds and/or immuno-modulating compounds.

Salts

The oligomeric compound comprised in this invention can be employed in a variety of pharmaceutically acceptable salts. As used herein, the term refers to salts that retain the desired biological activity of the herein identified compounds and exhibit minimal undesired toxicological effects. Non-limiting examples of such salts can be formed with organic amino acid and base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylene-diamine, D-glucosamine, tetraethylammonium, or ethylenediamine; or (c) combinations of (a) and (b); e.g., a zinc tannate salt or the like.

Prodrugs

In one embodiment of the invention the oligomeric compound may be in the form of a pro-drug. Oligonucleotides are by virtue negatively charged ions. Due to the lipophilic nature of cell membranes the cellular uptake of oligonucleotides are reduced compared to neutral or lipophilic equivalents. This polarity "hindrance" can be avoided by using the pro-drug approach (see e.g. Crooke, R. M. (1998) in Crooke, S. T. *Antisense research and Application*. Springer-Verlag, Berlin, Germany, vol. 131, pp. 103-140). In this approach the oligonucleotides are prepared in a protected manner so that the oligo is neutral when it is administered. These protection groups are designed in such a way that so they can be removed then the oligo is taken up be the cells. Examples of such protection groups are S-acetylthioethyl (SATE) or S-pivaloylthioethyl (t-butyl-SATE). These protection groups are nuclease resistant and are selectively removed intracellulary.

Conjugates

In one embodiment of the invention the oligomeric compound is linked to ligands/conjugates. It is way to increase the cellular uptake of antisense oligonucleotides. This conjugation can take place at the terminal positions 5'/3'-OH but the ligands may also take place at the sugars and/or the bases. In particular, the growth factor to which the antisense oligonucleotide may be conjugated, may comprise transferrin or folate. Transferrin-polylysine-oligonucleotide complexes or folate-polylysine-oligonucleotide complexes may be prepared for uptake by cells expressing high levels of transferrin or folate receptor. Other examples of conjugates/lingands are cholesterol moieties, duplex intercalators such as acridine, poly-L-lysine, "end-capping" with one or more nuclease-resistant linkage groups such as phosphoromonothioate, and the like.

The preparation of transferrin complexes as carriers of oligonucleotide uptake into cells is described by Wagner et al., *Proc. Natl. Acad. Sci. USA* 87, 3410-3414 (1990). Cellular delivery of folate-macromolecule conjugates via folate receptor endocytosis, including delivery of an antisense oligonucleotide, is described by Low et al., U.S. Pat. No. 5,108, 921. Also see, Leamon et al., *Proc. Natl. Acad. Sci.* 88, 5572 (1991).

Formulations

The invention also includes the formulation of one or more oligonucleotide compound as disclosed herein. Pharmaceutically acceptable binding agents and adjuvants may comprise part of the formulated drug. Capsules, tablets and pills etc. may contain for example the following compounds: microcrystalline cellulose, gum or gelatin as binders; starch or lactose as excipients; stearates as lubricants; various sweetening or flavouring agents. For capsules the dosage unit may contain a liquid carrier like fatty oils. Likewise coatings of sugar or enteric agents may be part of the dosage unit. The oligonucleotide formulations may also be emulsions of the active pharmaceutical ingredients and a lipid forming a micellar emulsion.

An oligonucleotide of the invention may be mixed with any material that do not impair the desired action, or with material that supplement the desired action. These could include other drugs including other nucleoside compounds.

For parenteral, subcutaneous, intradermal or topical administration the formulation may include a sterile diluent, buffers, regulators of tonicity and antibacterials. The active compound may be prepared with carriers that protect against degradation or immediate elimination from the body, including implants or microcapsules with controlled release properties. For intravenous administration the preferred carriers are physiological saline or phosphate buffered saline.

Preferably, an oligomeric compound is included in a unit formulation such as in a pharmaceutically acceptable carrier or diluent in an amount sufficient to deliver to a patient a therapeutically effective amount without causing serious side effects in the treated patient.

Administration

The pharmaceutical compositions of the present invention may be administered in a number of ways depending upon whether local or systemic treatment is desired and upon the area to be treated. Administration may be (a) oral (b) pulmonary, e.g., by inhalation or insufflation of powders or aerosols, including by nebulizer; intratracheal, intranasal, (c) topical including epidermal, transdermal, ophthalmic and to mucous membranes including vaginal and rectal delivery; or (d) parenteral including intravenous, intraarterial, subcutaneous, intraperitoneal or intramuscular injection or infusion; or intracranial, e.g., intrathecal or intraventricular, administration. In one embodiment the active oligo is administered IV, IP, orally, topically or as a bolus injection or administered directly in to the target organ.

Pharmaceutical compositions and formulations for topical administration may include transdermal patches, ointments, lotions, creams, gels, drops, sprays, suppositories, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Compositions and formulations for oral administration include but is not restricted to powders or granules, microparticulates, nanoparticulates, suspensions or solutions in water or non-aqueous media, capsules, gel capsules, sachets, tablets or minitablets. Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Delivery

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. Delivery of drug to tumour tissue may be enhanced by carrier-mediated delivery including, but not limited to, cationic liposomes, cyclodextrins, porphyrin derivatives, branched chain dendrimers, polyethylenimine polymers, nanoparticles and microspheres (Dass C R. J Pharm Pharmacol 2002; 54(1):3-27).

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels and suppositories. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Combination Drug

Oligonucleotides of the invention may be used to abolish the effects of HIF-1α induction by acute hypoxia induced by androgen withdrawal therapy in prostate cancer.

Oligonucleotides of the invention may also be conjugated to active drug substances, for example, aspirin, ibuprofen, a sulfa drug, an antidiabetic, an antibacterial or an antibiotic.

LNA containing oligomeric compounds are useful for a number of therapeutic applications as indicated above. In general, therapeutic methods of the invention include administration of a therapeutically effective amount of an LNA-modified oligonucleotide to a mammal, particularly a human.

In a certain embodiment, the present invention provides pharmaceutical compositions containing (a) one or more antisense compounds and (b) one or more other chemotherapeutic agents which function by a non-antisense mechanism. When used with the compounds of the invention, such chemotherapeutic agents may be used individually (e.g. mithramycin and oligonucleotide), sequentially (e.g. mithramycin and oligonucleotide for a period of time followed by another agent and oligonucleotide), or in combination with one or more other such chemotherapeutic agents or in combination with radiotherapy. All chemotherapeutic agents known to a person skilled in the art are here incorporated as combination treatments with compound according to the invention.

Anti-inflammatory drugs, including but not limited to nonsteroidal anti-inflammatory drugs and corticosteroids, antiviral drags, and immuno-modulating drugs may also be combined in compositions of the invention. Two or more combined compounds may be used together or sequentially.

In another embodiment, compositions of the invention may contain one or more antisense compounds, particularly oligonucleotides, targeted to a first nucleic acid and one or more additional antisense compounds targeted to a second nucleic acid target. Two or more combined compounds may be used together or sequentially.

Dosage

Dosing is dependent on severity and responsiveness of the disease state to be treated, and the course of treatment lasting from several days to several months, or until a cure is effected or a diminution of the disease state is achieved. Optimal dosing schedules can be calculated from measurements of drug accumulation in the body of the patient.

Optimum dosages may vary depending on the relative potency of individual oligonucleotides. Generally it can be estimated based on EC50s found to be effective in in vitro and in vivo animal models. In general, dosage is from 0.01 µg to 1 g per kg of body weight, and may be given once or more daily, weekly, monthly or yearly, or even once every 2 to 10 years or by continuous infusion for hours up to several months. The repetition rates for dosing can be estimated based on measured residence times and concentrations of the drug in bodily fluids or tissues. Following successful treatment, it may be desirable to have the patient undergo maintenance therapy to prevent the recurrence of the disease state.

Uses

The LNA containing oligomeric compounds of the present invention can be utilized for as research reagents for diagnostics, therapeutics and prophylaxis. In research, the antisense oligonucleotides may be used to specifically inhibit the synthesis of HIF-1α genes in cells and experimental animals thereby facilitating functional analysis of the target or an appraisal of its usefulness as a target for therapeutic intervention. In diagnostics the antisense oligonucleotides may be used to detect and quantitate HIF-1α expression in cell and tissues by Northern blotting, in-situ hybridisation or similar techniques. For therapeutics, an animal or a human, suspected of having a disease or disorder, which can be treated by modulating the expression of HIF-1α is treated by administering antisense compounds in accordance with this invention. Further provided are methods of treating an animal particular mouse and rat and treating a human, suspected of having or being prone to a disease or condition, associated with expression of HIF-1α by administering a therapeutically or prophylactically effective amount of one or more of the antisense compounds or compositions of the invention.

Methods

The methods of the invention is preferably employed for treatment or prophylaxis against diseases caused by a disease. One embodiment of the invention involves a method of inhibiting the expression of HIF-1α, in cells or tissues comprising contacting said cells or tissues with the compound of the invention so that expression of HIF-1α is inhibited. Furthermore, another embodiment is a method of modulating expression of a gene involved in a disease comprising contacting the gene or RNA from the gene with an oligomeric compound wherein said compound has a sequence comprising at least an 8 nucleobase portion of SEQ ID NO: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114 or 115 whereby gene expression is modulated. These compounds may comprise one or more LNA units. The compound may hybridizes with messenger RNA of the gene to inhibit expression thereof. Another embodiment is a method of treating a mammal suffering from or susceptible from a cancer disease, comprising, administering to the mammal an therapeutically effective amount of an oligonucleotide targeted to HIF-1α that comprises one or more LNA units. The described methods may target a common cancers, as e.g. primary and metastatic breast, colorectal, prostate, pancreas, other GI-cancers, lung, cervical, ovarian, brain, head and neck, cervix, colon, liver, thyroid, kidney, testes, stomach, intestine, bowel, esophagus, spinal cord, sinuses, bladder or urinary tract tumors, as well as pre-eclampsia, inflammatory bowel disease and Alzheimers disease. The method may also modulate angiogenesis as well as red blood cell proliferation, cellular proliferation, iron metabolism, glucose and energy metabolism, pH regulation, tissue invasion, apoptosis, multi-drug resistance, cellular stress response or matrix metabolism comprising contacting a cell with the antisense compound of claim the invention so that the cell is modulated.

All documents mentioned herein are incorporated herein by reference.

EXAMPLES

The present invention has been described with specificity in accordance with certain of its preferred embodiments. Therefore, the following examples serve only to illustrate the invention and are not intended to limit the same.

Example 1

Monomer Synthesis

Preparation of the monomers shown in Scheme 2 in which Y and X are —O— and Z and Z* are protected —O— is described in great detail in the reference, Koshkin et al, *J. Org. Chem.*, 2001, 66, 8504-8512; Sørensen et al., J. Am. Chem. Soc., 2002, 124 (10), 2164-2176; Pedersen et al., Synthesis, 2002, 6, 802-809 and references found therein, where the protection groups of Z and Z* are respectively oxy-N,N-diisopropyl-O-(2-cyanoethyl)phosphoramidite and dimethoxytrityloxy. The preparation of monomers of the Scheme 2 in which X is —O— and Y is —S— and —N(CH₃)— is described in Rosenbohm, et al. Org. Biomol. Chem., 2003, 1, 655-663.

Example 2

LNA Oligonucleotide Synthesis

All oligonucleotide syntheses are carried out in 1 µmol scale on a MOSS Expedite instrument platform. The synthesis procedures are essentially carried out as described in the instrument manual. The LNA monomers used were synthesised according Koshin A. A. et al J. Org. Chem., 2001, 66, 8504-8512.

Preparation of the LNA Succinyl Hemiester

5'-O-Dmt-3'-hydroxy-LNA monomer (500 mg), succinic anhydride (1.2 eq.) and DMAP (1.2 eq.) were dissolved in DCM (35 mL). The reaction was stirred at room temperature overnight. After extractions with NaH$_2$PO$_4$ 0.1 M pH 5.5 (2×) and brine (1×), the organic layer was further dried with anhydrous Na$_2$SO$_4$ filtered and evaporated. The hemiester derivative was obtained in 95% yield and was used without any further purification.

Preparation of the LNA-CPG Resin

The above prepared hemiester derivative (90 µmol) was dissolved in a minimum amount of DMF, DIEA and pyBOP (90 µmol) were added and mixed together for 1 min. This pre-activated mixture was combined with LCAA-CPG (500 Å, 80-120 mesh size, 300 mg) in a manual synthesizer and stirred. After 1.5 h at room temperature, the support was filtered off and washed with DMF, DCM and MeOH. After drying the loading was determined, and resulted to be 57 µmol/g.

Phosphorothioate Cycles

5'-O-Dmt (A(bz), C(bz), G(ibu), and T) linked to CPG (controlled pore glass) were deprotected using a solution of 3% trichloro acetic acid (v/v) in dichloromethane. The resin is washed with acetonitrile. Coupling of phosphoramidites (A(bz), G(ibu), 5-methyl-C(bz)) or T-β-cyanoethylphosphoramidite) is performed by using a solution of 0.08 M of the 5'-O-Dmt-protected amidite in acetonitrile and activation is done by using DCI (4,5-dicyanoimaidazole) in acetonitrile (0.25 M). Coupling is carried out in 2 minutes. Thiolation is carried out by using Beaucage reagent (0.05 M in acetonitrile) and is allowed to react for 3 minutes. The support is thoroughly washed with acetonitrile and the subsequent capping capping is carried out by using a solution of and acetic anhydride in THF (CAP A) and N-methylimidazole/pyridine/THF (1:1:8) (CAP B) to cap unreacted 5'-hydroxyl groups. The capping step is then repeated and the cycle is concluded by acetonitrile washing.

LNA Cycles

5'-O-Dmt (locA(bz), locC(bz), locG(ibu) or locT) linked to CPG (controlled pore glass) is deprotected by using the same procedure as above. Coupling is performed by using 5'-Dmt (locA(bz), locC(bz), locG(ibu) or locT)-β-cyanoethylphosphoramidite (0.1 M in acetonitrile) and activation is done by DCI (0.25 M in acetonitrile). Coupling is prolonged to 7 minutes. Capping is done by using acetic anhydride in THF (CAP A) and a solution of N-methylimidazole/pyridine/THF (1:1:8) (CAP B) for 30 sec. The phosphite triester is oxidized to the more stable phosphate triester by using a solution of I$_2$ and pyridine in THF for 30 sec. The support is washed with acetonitrile and the capping step is repeated. The cycle is concluded by thorough acetonitrile wash. Abbreviations: Dmt: Dimethoxytrityl and DCI: 4,5-Dicyanoimidazole.

Oligonucleotide Cleavage and Deprotection

The oligomers are cleaved from the support and the β-cyanoethyl protecting group removed by treating the support with 35% NH$_4$OH 1 h at room temperature. The support is filtered off and the base protecting groups are removed by raising the temperature to 65° C. for 4 hours. The oligosolution is then evaporated to dryness.

Oligonucleotide Purification

The oligos are either purified by (reversed-phase) RP-HPLC or (anion exchange) AIE.

RP-HPLC:

| Column: | VYDAC™ cat. No. 218TP1010 (vydac) | | | | | |
|---|---|---|---|---|---|---|
| Flow rate: | 3 mL/min | | | | | |
| Buffer: | A | 0.1M ammonium acetate pH 7.6 | | | | |
| | B | acetonitrile | | | | |
| Gradient: | | | | | | |
| Time | 0 | 10 | 18 | 22 | 23 | 28 |
| B % | 0 | 5 | 30 | 100 | 100 | 0 |

IE:

| Column: | Resource™ 15Q (amersham pharmacia biotech) | | | | | |
|---|---|---|---|---|---|---|
| Flow rate: | 1.2 mL/min | | | | | |
| Buffer: | A | 0.1M NaOH | | | | |
| | B | 0.1M NaOH, 2.0M NaCl | | | | |
| Gradient: | | | | | | |
| Time | 0 | 1 | 27 | 28 | 32 | 33 |
| B % | 0 | 25 | 55 | 100 | 100 | 0 |

Abbreviations

| Dmt: | Dimethoxytrityl |
|---|---|
| DCI: | 4,5-Dicyanoimidazole |
| DMAP: | 4-Dimethylaminopyridine |
| DCM: | Dichloromethane |
| DMF: | Dimethylformamide |
| THF: | Tetrahydrofurane |
| DIEA: | N,N-diisopropylethylamine |
| PyBOP: | Benzotriazole-1-yl-oxy-tris-pyrrolidino-phosphonium hexafluorophosphate |
| Bz: | Benzoyl |
| Ibu: | Isobutyryl |
| Beaucage: | 3H-1,2-Benzodithiole-3-one-1,1-dioxide |
| A(bz), C(bz), G(ibu) or T: | LNA-monomers (LNA-locked nucleic acid) |

Example 3

Cell Culture

Antisense compounds and their effect on target nucleic acid expression can be tested in any of a variety of cell types provided that the target nucleic acid or protein is present at measurable levels. This can be routinely determined using, for example, RT-PCR or Northern blot or Western blot analysis. The following cell types are provided for illustrative purposes, but other cell types can be routinely used, provided that the target is expressed in the cell type chosen.

Cell lines were cultured in the appropriate medium as described below and maintained at 37° C. at 95-98% humidity and 5% $CO_2$. Cells were routinely passaged 2-3 times weekly.

U87-MG: The human glioblastoma cell line U87-MG was cultured in Modified Eagle Medium (MEM) with Earle's salts and 10% Fetal Calf Serum (FCS)

U373: The human glioblastoma cell line U373 was cultured in Modified Eagle Medium (MEM) with Earle's salts and 10% Fetal Calf Serum (FCS)

15PC3: The human prostate cancer cell line 15PC3 was kindly donated by Dr. F. Baas, Neurozintuigen Laboratory, AMC, The Netherlands and was cultured in DMEM (Sigma)+10% fetal bovine serum (FBS)+Glutamax I+gentamicin Anaerobic cell culture: To monitor changes in HIF expression under hypoxic conditions, cells were cultured under anaerobic conditions at an $O_2$ level of 0.1-1.5% in an incubation bag (Merck) with Anaerocult (Merck) added to chemically bind $O_2$. Anaerobic conditions were obtained within 1-2 hours. Cells were subjected to anoxia for 6 or 18 hours.

Example 4

Treatment with Antisense Oligonucleotide

The cells (described above) were treated with oligonucleotide using the cationic liposome formulation LipofectAMINE 2000 (Gibco) as transfection vehicle. Cells were seeded in 100 mm×20 mm cell culture petri dishes (Corning) or 6-well plates (NUNC) and treated when 90% confluent. Oligo concentrations used ranged from 1 nM to 400 nM final concentration. Formulation of oligo-lipid complexes was carried out according to the manufacturers instructions using serum-free MEM and a final lipid concentration of 5 μg/ml in 6 ml total volume. Cells were incubated at 37° C. for 4 or 24 hours and treatment was stopped by removal of oligo-containing culture medium. Cells were washed and serum-containing MEM was added. After oligo treatment cells were either allowed to recover for 18 hours before they were subjected to anoxia for 6 hours or directly subjected to anoxia for 18 hours.

Example 5

Extraction of Total RNA

Total RNA was isolated either using RNeasy mini kit (e.g. Qiagen cat. no. 74104) or using the Trizol reagent (e.g. Life technologies cat. no. 15596). For RNA isolation from cell lines, RNeasy is the preferred method and for tissue samples Trizol is the preferred method. Total RNA was isolated from cell lines using the RNeasy mini kit (Qiagen) according to the protocol provided by the manufacturer. Tissue samples were homogenised using an Ultra Turrax T8 homogeniser (e.g. IKA Analysen technik) and total RNA was isolated using the Trizol reagent protocol provided by the manufacturer.

Example 6

First Strand cDNA Synthesis

First strand synthesis was performed using OmniScript Reverse Transcriptase kit (cat#205113, Qiagen) according to the manufacturers instructions.

For each sample 0.5 μg total RNA was adjusted to 12 it each with RNase free $H_2O$ and mixed with 2 μl poly $(dT)_{12-18}$ (2.5 μg/ml) (Life Technologies, GibcoBRL, Roskilde, DK), 2 μl dNTP mix (5 mM each dNTP), 2 μl 10× Buffer RT, 1 μl RNAguard™Rnase INHIBITOR (33.3 U/ml), (cat#27-0816-01, Amersham Pharmacia Biotech, Hørsholm, DK) and 1 μl OmniScript Reverse Transcriptase (4 U/μl) followed by incubation at 37° C. for 60 minutes and heat inactivation of the enzyme at 93° C. for 5 minutes.

Example 7

Antisense Modulation of HIF-1α Expression Analysis

Antisense modulation of HIF-1α expression can be assayed in a variety of ways known in the art. For example, HIF-1α mRNA levels can be quantitated by, e.g., Northern blot analysis, competitive polymerase chain reaction (PCR), or real-time PCR. Real-time quantitative PCR is presently preferred. RNA analysis can be performed on total cellular RNA or mRNA.

Methods of RNA isolation and RNA analysis such as Northern blot analysis is routine in the art and is taught in, for example, Current Protocols in Molecular Biology, John Wiley and Sons.

Real-time quantitative (PCR) can be conveniently accomplished using the commercially available iQ Multi-Color Real Time PCR Detection System, available from BioRAD.
Real-Time Quantitative PCR Analysis of Ha-ras mRNA Levels Quantitation of mRNA levels was determined by real-time quantitative PCR using the iQ Multi-Color Real Time PCR. Detection System (BioRAD) according to the manufacturers instructions.

Real-time Quantitative PCR is a technique well known in the art and is taught in for example Heid et al. Real time quantitative PCR, Genome Research (1996), 6: 986-994.

Platinum Quantitative PCR SuperMix UDG 2×PCR master mix was obtained from Invitrogen cat#11730. Primers and TaqMan® probes were obtained from MWG-Biotech AG, Ebersberg, Germany Probes and primers to human HIF-1α were designed to hybridise to a human Ha-ras sequence, using published sequence information (GenBank accession number NM_001530, incorporated herein as SEQ ID NO:1).

For human HIF-1α the PCR primers were:
forward primer: 5' CTCATCCAAGAAGCCCTAACGTGTT 3' (final concentration in the assay; 0.9 µM) (SEQ ID NO: 116) reverse primer: 5' GCTTTCTCTGAGCATTCTG-CAAAGC 3' (final concentration in the assay, 0.9 µM) (SEQ ID NO: 117) and the PCR probe was: 5' FAM-CCTCAG-GAACTGTAGTTCTTTGACTCAAAGCGACA-TAMRA 3' (final concentration in the assay; 0.1 µM) (SEQ ID NO: 118)

Glyceraldehyde-3-phosphate dehydrogenase (GAPDH) mRNA quantity was used as an endogenous control for normalizing any variance in sample preparation. The sample content of human GAPDH mRNA was quantified using the human GAPDH ABI Prism Pre-Developed TaqMan Assay Reagent (Applied Biosystems cat. no. 4310884E) according to the manufacturers instructions.

For quantification of mouse GAPDH mRNA the following primers and probes were designed: Sense primer 5' aaggct-gtgggcaaggtcatc 3' (0.3 µM final concentration), antisense primer 5' gtcagatccacgacggacacatt (0.6 µM final concentration), TaqMan probe 5' FAM-gaagctcactggcatggcatggcatc-cgtgttc-TAMRA 3' (0.2 µM final concentration).
Real Time PCR The cDNA from the first strand synthesis performed as described in example 8 was diluted 2-20 times, and analyzed by real time quantitative PCR. The primers and probe were mixed with 2× Platinum Quantitative PCR SuperMix UDG (cat. #11730, Invitrogen) and added to 3.3 µl cDNA to a final volume of 25 µl. Each sample was analysed in triplicates. Assaying 2 fold dilutions of a cDNA that had been prepared on material purified from a cell line expressing the RNA of interest generated standard curves for the assays. Sterile H$_2$O was used instead of cDNA for the no template control. PCR program: 50° C. for 2 minutes, 95° C. for 10 minutes followed by 40 cycles of 95° C., 15 seconds, 60° C., 1 minutes.

Relative quantities of target mRNA sequence were determined from the calculated Threshold cycle using the iCycler iQ Real-time Detection System software.

Example 8

Western Blot Analysis of HIF-1α Protein Levels

Protein levels of HIF-1α can be quantitated in a variety of ways well known in the art, such as immunoprecipitation, Western blot analysis (immunoblotting), ELISA, RIA (Radio Immuno Assay) or fluorescence-activated cell sorting (FACS). Antibodies directed to HIF-1α can be identified and obtained from a variety of sources, such as Upstate Biotechnologies (Lake Placid, USA), Novus Biologicals (Littleton, Colo.), Santa Cruz Biotechnology (Santa Cruz, Calif.) or can be prepared via conventional antibody generation methods.

To measure the effect of treatment with antisense oligonucleotides against HIF-1α, protein levels of HIF1-α in treated and untreated cells were determined using Western blotting.

After treatment with oligonucleotide as described above, cell were harvested by scraping with a rubber policeman in ice-cold phosphate-buffered saline (PBS) containing 0.37 mg/ml of the protease inhibitor phenyl methyl sulfonyl fluoride (PMSF).

The harvested cells were washed in 1 mL PBS containing PMSF as described above and cell pellets were kept frozen at −80° C.

For protein extraction, frozen cell pellets were dissolved in 3 volumes of ice-cold lysis buffer (50 mM Tris, pH 7.5, 150 mM NaCl, 1% Non-idet P 40 (NP-40), 0.1% SDS, 1% (w/v) natrium-deoxycholat, 1 mM dithiothreitol (DTT), Complete protein inhibitor cocktail (Boehringer Mannheim)). The samples were sonicated 2-3 times a 5-10 seconds in a Vibra Cell 50 sonicator (Sonics & Materials Inc.). The lysate was stored at −80° C. until further use.

Protein concentration of the protein lysate was determined using the BCA Protein Assay Kit (Pierce) as described by the manufacturer.
SDS Gel Electrophoresis:

Protein samples prepared as described above were thawed on ice and denatured at 70° C. for 10 min.

Samples were loaded on 1.0 mm 10% NuPage Bis-Tris gel (NOVEX) and gels were run in running buffer, either NuPage MES SDS Running Buffer or NuPage MOPS SDS Running Buffer (both NOVEX) depending on desired separation of proteins in an Xcell II Mini-cell electrophoresis module (NOVEX).

In the inner chamber of the electrophoresis module NuPage Antioxidant (NOVEX) was added to the running buffer at a final concentration of 2.5 µl/ml. For size reference, SeeBlue Plus2 Prestained Standard (Invitrogen) was loaded on the gel. The electrophoresis was run at 160 V for 2 hours.
Semi-Dry Blotting:

After electrophoresis, the separated proteins were transferred to a polyvinyliden difluoride (PVDF) membrane by semi-dry blotting. The gel was equilibrated in NuPage Transfer Buffer (NOVEX) until blotted. The blotting procedure was carried out in a Trans-blot SD Semi-Dry transfer cell (BioRAD) according to the manufacturers instructions. The membrane was stored at 4° C. until further use.
Immunodetection:

To detect the desired protein, the membrane was incubated with either polyclonal or monoclonal antibodies against the protein. The membrane was blocked in blocking buffer (2.5% skim milk powder and 5% BSA dissolved in TS-buffer (150 mM NaCl, 10 mM Tris·base pH 7.4)) for 1 hour with agitation. The membrane was then washed 2×15 min. in TS-buffer at room temperature and incubated over night with primary antibody in TS-Tween20-buffer with 0.1% NaN$_3$ at 4 C. The following primary monoclonal antibodies and concentrations/dilutions were used: Mouse-anti-Glut1 (from T. Ploug, The Panum Institute, Copenhagen) 1:20, mouse-anti-HIF-1α (H72320, Transduction Laboratories) 1 µg/ml, mouse-anti-α-tubulin (T-9026, Sigma) 1:10.000. After incubation with the primary antibody the membrane was washed in TS-Tween20-buffer for 15 minutes followed by 2 additional washes of 5 minutes each with agitation at room temperature. Subsequently the membrane was incubated with a 1:5000 dilution of the secondary antibody, peroxidase conjugated polyclonal goat-anti-mouse-immunoglobulins (P0447, DAKO A/S) for 1 hour at room temperature. The membrane was then washed in TS-Tween20-buffer for 15 minutes followed by 3 additional of washes 5 minutes each with agitation at room temperature. After the last wash the membrane was incubated with ECL+ Plus (Amersham), for 5 minutes followed by an immediate scanning with a STORM 840 (Molecular Dynamics Inc.). The membrane was stripped in stripping-buffer (100 mM 2-mercapto-ethanol, 2% SDS, 62.5 mM Tris-base) pH 6.7 by incubation with low agitation for 30 minutes at 50 C. After wash in TS-Tween20-buffer 2×10 minutes at room temperature, the membrane was dried and sealed in a plastic bag and stored at 4 C. The Protein expression levels were quantified relative to expression of a housekeeping protein using Image Quant version 5.0 software (Molecular Dynamics Inc).

Example 9

Antisense Inhibition of Human HIF-1α Expression by Oligonucleotides

In accordance with the present invention, a series of oligonucleotides were designed to target different regions of the human HIF-1α RNA, using published sequences (GenBank accession number NM_001530, incorporated herein as SEQ ID NO: 1 and FIG. 7). The oligonucleotides 16 nucleotides in length are shown in Table 1 and are having a SEQ ID NO. The oligonucleotides are designed so they are to be particularly potent as antisense oligonucleotides, particularly when synthesised using artificial nucleotides such as LNA or phosphorothioates etc. "Target site" indicates the first nucleotide number on the particular target sequence to which the oligonucleotide binds. The compounds were analysed for their effects on HIF-1α protein levels by Western blot analysis as described in other examples herein.

TABLE 1

Inhibition of human HIF-1α protein levels antisense oligonucleotides

| SEQ ID NO./ Cureon no. | % Inhibition 100 Nm oligo | Target site | Oligo Sequence 5'-3' | Oligo Design 5'-3' |
|---|---|---|---|---|
| SEQ ID NO 2/ 2651 | 92 | 234 | GCGATGTCTTCACGGC | $G_sC_sG_sA_st_sg_st_sc_st_st_sc_sa_sC_sG_sC$ |
| SEQ ID NO 3/ 2627 | 94 | 2256 | TGGTGAGGCTGTCCGA | $T_sG_sG_sT_sg_sa_sg_sg_sc_st_sg_st_sC_sC_sG_sA$ |
| SEQ ID NO 4 | | 251 | ATGGTGAATCGGTCCC | |
| SEQ ID NO 5 | | 250 | TGGTGAATCGGTCCCC | |
| SEQ ID NO 6 | | 49 | AGGTGGCTTGTCAGGG | |
| SEQ ID NO 7 | | 231 | ATGTCTTCACGGCGGG | |
| SEQ ID NO 8 | | 233 | CGATGTCTTCACGGCG | |
| SEQ ID NO 9 | | 2017 | GGCTTGCGGAACTGCT | |
| SEQ ID NO 10 | | 1471 | TTGTGTCTCCAGCGGC | |
| SEQ ID NO 11 | | 6 | CGAAGAGAGTGCTGCC | |
| SEQ ID NO 12/ 2654 | 96 | 153 | AGGCAAGTCCAGAGGT | $A_sG_sG_sC_sa_sa_sg_st_sc_sc_sa_sg_sA_sG_sG_sT$ |
| SEQ ID NO 13 | | 1937 | GCTAACATCTCCAAGT | |
| SEQ ID NO 14 | | 1965 | GAAGTCATCATCCATT | |
| SEQ ID NO 15 | | 1744 | GTGTCTGATCCTGAAT | |
| SEQ ID NO 16 | | 1821 | ATCCACATAAAAACAA | |
| SEQ ID NO 17 | | 2050 | CTGTAACTGTGCTTTG | |
| SEQ ID NO 18 | | 2182 | TAGGAGATGGAGATGC | |
| SEG ID NO 19 | | 2317 | CGTTAGGGCTTCTTGG | |
| SEQ ID NO 20 | | 2506 | TCCAAGAAAGTGATGT | |
| SEQ ID NO 21 | | 2621 | CCACTTTCATCCATTG | |
| SEQ ID NO 22/ 2655 | 93 | 2680 | TTCTGCTGCCTTGTAT | $T_sT_sC_sT_sg_sc_st_sg_sc_sc_st_st_sG_sT_sA_sT$ |
| SEQ ID NO 23/ 2656 | 93 | 2783 | TTTAGGTAGTGAGCCA | $T_sT_sT_sA_sg_sg_st_sa_sg_st_sg_sa_sG_sC_sC_sA$ |

TABLE 1-continued

Inhibition of human HIF-1α protein levels antisense oligonucleotides

| SEQ ID NO./ Cureon no. | % Inhibition 100 Nm oligo | Target site | Oligo Sequence 5'-3' | Oligo Design 5'-3' |
|---|---|---|---|---|
| SEQ ID NO 24 | | 2837 | GCAGTATTGTAGCCAG | |
| SEQ ID NO 25 | | 3067 | TATTGGCATCTTCTTA | |
| SEQ ID NO 26 | | 3100 | TGATGAAAGGTTACTG | |
| SEQ ID NO 27 | | 3169 | GGCAAAGCATTATTAT | |
| SEQ ID NO 28 | | 3356 | AACCATACAGCATTTA | |
| SEQ ID NO 29 | | 3360 | AATAAACCATACAGCA | |
| SEQ ID NO 30 | | 3426 | TGCCACATACCTTCTA | |
| SEQ ID NO 31 | | 3437 | ATCCAAATAAATGCCA | |
| SEQ ID NO 32 | | 3531 | CATAAACTTCCACAAC | |
| SEQ ID NO 33 | | 170 | GCGGAGAAGAGAAGGA | |
| SEQ ID NO 34 | | 3582 | CCAACAGGGTAGGCAG | |
| SEQ ID NO 35 | | 3704 | AATAGCGACAAAGTGC | |
| SEQ ID NO 36 | | 3845 | AACCACAAAGAGCAAA | |
| SEQ ID NO 37 | | 2369 | TTTAGTTCTTCCTCAG | |
| SEQ ID NO 38 | | 2848 | ACCAAGTTTGTGCAGT | |
| SEQ ID NO 38 | | 2413 | TTTTTCGCTTTCTCTG | |
| SEQ 1D NO 40 | | 2919 | CAGCATTAAAGAACAT | |
| SEQ ID NO 41 | | 2986 | AAAATGATGCTACTGC | |
| SEQ ID NO 42 | | 2720 | TGATCCAAAGCTCTGA | |
| SEQ ID NO 43 | | 286 | TCTTTTTCTTGTCGTT | |
| SEQ ID NO 44 | | 3032 | ATAAACTCCCTAGCCA | |
| SEQ ID NO 45 | | 3228 | GTAACTGCTGGTATTT | |
| SEQ ID NO 46 | | 3299 | TAACAATTTCATAGGC | |
| SEQ ID NO 47 | | 3490 | GCTGGCAAAGTGACTA | |
| SEQ ID NO 48 | | 3610 | TTTACAGTCTGCTCAA | |
| SEQ ID NO 49 | | 3677 | CATTGTATTTTGAGCA | |
| SEQ ID NO 50 | | 3786 | TTTACTGTGACAACTA | |
| SEQ ID NO 51 | | 3874 | AACAAAACAATACAGT | |
| SEQ ID NO 52 | | 384 | TGGCAACTGATGAGCA | |
| SEQ ID NO 53/ 2657 | 87 | 479 | TCACCAGCATCCAGAA | $T_sC_sA_sC_sc_sa_sg_sc_sa_st_sc_sc_sA_sG_sA_sA$ |
| SEQ ID NO 54/ 2658 | 84 | 917 | ATCAGCACCAAGCAGG | $A_sT_sC_sA_sg_sc_sa_sc_sc_sa_sa_sg_sC_sA_sG_sG$ |
| SEQ ID NO 55/ 2659 | 95 | 1177 | TGGCAAGCATCCTGTA | $T_sG_sG_sC_sa_sa_sg_sc_sa_st_sc_sc_sT_sG_sT_sA$ |
| SEQ ID NO 56/ 2660 | 93 | 1505 | TCTGTGTCGTTGCTGC | $T_sC_sT_sG_st_sg_st_sc_sg_st_st_sg_sC_sT_sG_sC$ |
| SEQ ID NO 57 | | 2095 | TGGTGGCATTAGCAGT | |

TABLE 1-continued

Inhibition of human HIF-1α protein levels antisense oligonucleotides

| SEQ ID NO./ Cureon no. | % Inhibition 100 Nm oligo | Target site | Oligo Sequence 5'-3' | Oligo Design 5'-3' |
|---|---|---|---|---|
| SEQ ID NO 58 | | 2116 | CATCAGTGGTGGCAGT | |
| SEQ ID NO 59/ 2661 | 86 | 2223 | TGGTGATGATGTGGCA | $T_sG_sT_sg_sa_st_sg_sa_st_sg_st_sG_sG_sC_sA$ |
| SEQ ID NO 60/ 2662 | 79 | 2477 | TCGTCTGGCTGCTGTA | $T_sC_sG_sT_sc_st_sg_sg_sc_st_sg_sc_sT_sG_sT_sA$ |
| SEQ ID NO 61/ 2663 | 85 | 2553 | TTGCTCCATTCCATTC | $T_sT_sG_sC_st_sc_sc_sa_st_st_sc_sc_sA_sT_sT_sC$ |
| SEQ ID NO 62 | | 98 | AAGCGGGCGGCAATCG | |
| SEQ ID NO 63 | | 349 | ATTCTTTACTTCGCCG | |
| SEQ ID NO 64 | | 412 | CAAGATGCGAACTCAC | |
| SEQ ID NO 65 | | 516 | ATTCATCTGTGCTTTC | |
| SEQ ID NO 66 | | 574 | TGTCACCATCATCTGT | |
| SEQ ID NO 67 | | 747 | GCTTCGCTGTGTGTTT | |
| SEQ ID NO 68 | | 638 | TGTCCAGTTAGTTCAA | |
| SEQ ID NO 69 | | 700 | TGTGTGTAAGCATTTC | |
| SEQ ID NO 70 | | 809 | GCAGACTTTATGTTCA | |
| SEQ ID NO 71 | | 871 | GTTGGTTACTGTTGGT | |
| SEQ ID NO 72 | | 968 | TTGCTATCTAAAGGAA | |
| SEQ ID NO 73 | | 1104 | ATCAGAGTCCAAAGCA | |
| SEQ ID NO 74 | | 1057 | GTTCTTCTGGCTCATA | |
| SEQ ID NO 75 | | 1003 | ATTTCATATCCAGGCT | |
| SEQ ID NO 76 | | 1163 | TACTGTCCTGTGGTGA | |
| SEQ ID NO 77 | | 1221 | TATGACAGTTGCTTGA | |
| SEQ ID NO 78 | | 1284 | AATACCACTCACAACG | |
| SEQ ID NO 79 | | 1322 | TCTGTTTGTTGAAGGG | |
| SEQ ID NO 80 | | 1383 | AACTTTGGTGAATAGC | |
| SEQ ID NO 81 | | 1440 | TAAAGCATCAGGTTCC | |
| SEQ ID NO 82 | | 1559 | GGGAGCATTACATCAT | |
| SEQ ID NO 83 | | 1613 | GTGGGTAATGGAGACA | |
| SEQ ID NO 84 | | 1669 | CTTCTTGATTGAGTGC | |
| SEQ ID NO 85 | | 1702 | GTGACTCTGGATTTGG | |
| SEQ ID NO 86 | | 1783 | CAGGTGAACTTTGTCT | |
| SEQ ID NO 87 | | 1804 | ATTCACTGGGACTATT | |
| SEQ ID NO 88 | | 1887 | TGCTTCTGTGTCTTCA | |
| SEQ ID NO 114/ Cur2652 | 97 | 3091 | GTTACTGCCTTCTTAC | $G_sT_sT_sA_sc_st_sg_sc_sc_st_st_sc_sT_sT_sA_sC$ |
| SEQ ID NO 115/ Cur2653 | 90 | 293 | CCGGCGCCCTCCATGG | $C_sC_sG_sG_sc_sg_sc_sc_sc_st_sc_sc_sA_sT_sG_sG$ |

The sequences that demonstrated at least 20% inhibition of HIF-1α expression in this experiment are preferred (see also FIGS. 1-9). The target sites to which these preferred sequences are complementary are herein referred to as "hot spots" and are therefore preferred sites for targeting by compounds of the present invention.

Example 10

Antisense Inhibition of HIF-1α by Phosphorothioate, LNA Containing Oligonucleotides or Chimeric Oligonucleotides Having at Least One LNA Segments and at Least One Phosphorothioate Segment In accordance with the present invention, a second series of antisense oligonucleotides were also synthesized (table 2). These series of compounds are full-modified phosphorothioate oligonucleotide, full modified LNA oligonucleotide or a chimeric oligonucleotides 16 nucleotides in length targeting two different sites. The chimeric oligonucleotides are a "gapmer" (GM), "headmen" (WM5) or "tailmer" (WM3) composed of a region consisting of phosphoroptioates (P S) which is flanked on one or both side(s) with a LNA segment. These segments are composed of oxy-LNA nucleotides. Some the oligonucleotides also had a fluorescent colour (FAM) incorporated. Mismatch oligonucleotides were also designed (MM). All cytosines in oxy-LNA are methylated at the CS position of the nucleobases. The compounds were analysed for their effect on HIF-1α protein levels by western blotting as described in other examples herein. "Target site" indicates the first nucleotide number on the particular target sequence to which the oligonucleotide binds.

TABLE 2

Inhibition of human HIF-1α protein levels by phosphorothioate oligonucleotides, LNA containing oligonucleotides or chimeric oligonucleotides having one or two LNA segment(s) and one phosphorothioate segment

| Name | SEQ NO | % inhibition 100 nM oligo | Target Site & Design | Sequence & Design 5'-3' |
|---|---|---|---|---|
| Cur0805 | SEQ ID 89 | 24 | 234 FM | GCGATGTCTTCACGGC |
| Cur0806 | SEQ ID 90 | 21 | 234 PS | $g_s c_s g_s a_s t_s g_s t_s c_s t_s c_s a_s c_s g_s g_s c$ |
| Cur0807 | SEQ ID 91 | | 234 GM | GCGA$_s t_s g_s t_s c_s t_s t_s c_s a_s$CGGC |
| Cur0808 | SEQ ID 92 | | 234 FAM | FAM-GCGA$_s t_s g_s t_s c_s t_s t_s c_s a_s$CGGC |
| Cur0809 | SEQ ID 93 | 34 | 234 WM5 | GCGATGTC$_s t_s t_s c_s a_s c_s g_s g_s$c |
| Cur0810 | SEQ ID 94 | 54 | 234 WM3 | $g_s c_s g_s a_s t_s g_s t_s c_s$TTCACGGC |
| Cur0811 | SEQ ID 95 | 24 | 2256 FM | TGGTGAGGCTGTCCGA |
| Cur0812 | SEQ ID 96 | | 2256 PS | $t_s g_s g_s t_s g_s a_s g_s g_s c_s t_s g_s t_s c_s c_s g_s a$ |
| Cur0813 | SEQ ID 97 | 86 | 2256 GM | TGGT$_s g_s a_s g_s g_s c_s t_s g_s t_s$CCGA |
| Cur0814 | SEQ ID 98 | | 2256 FAM | FAM-TGGT$_s g_s a_s g_s g_s c_s t_s g_s t_s$CCGA |
| Cur0815 | SEQ ID 99 | | 2256 WM5 | TGGTGAGG$_s c_s t_s g_s t_s c_s c_s g_s$a |
| Cur0816 | SEQ ID 100 | 37 | 2256 WM3 | $t_s g_s g_s t_s g_s a_s g_s g_s$CTGTCCGA |
| Cur0959 | SEQ ID 101 | | 234 MM1 | GCGAt$_s c_s t_s c_s t_s t_s c_s a_s$GGGC |
| Cur0960 | SEQ ID 102 | | 234 MM2 | GCGTt$_s g_s t_s c_s a_s t_s c_s a_s$CGGC |
| Cur0961 | SEQ ID 103 | | 2256 MM1 | TGGTg$_s a_s g_s c_s c_s t_s g_s t_s$CGGA |
| Cur0962 | SEQ ID 104 | | 2256 MM2 | TGCTg$_s a_s g_s g_s g_s t_s g_s t_s$CCGA |
| Cur2627 | SEQ ID 3 | 94 | 2256 GM | T$_s$G$_s$G$_s$T$_s g_s a_s g_s g_s c_s t_s g_s t_s$C$_s$C$_s$G$_s$A |
| Cur2628 | SEQ ID 105 | 95 | 2256 GM | T$_s$G$_s$G$_s t_s g_s a_s g_s g_s c_s t_s g_s t_s$C$_s$C$_s$G$_s$A |
| Cur2629 | SEQ ID 106 | 96 | 2256 GM | T$_s$G$_s$G$_s t_s g_s a_s g_s g_s c_s t_s g_s t_s$C$_s$C$_s$G$_s$a |
| Cur2630 | SEQ ID 107 | 95 | 2256 GM | T$_s$G$_s$G$_s$T$_s g_s a_s g_s g_s c_s t_s g_s t_s$C$_s$C$_s$G$_s$a |
| Cur2631 | SEQ ID 108 | 95 | 2256 GM | T$_s$G$_s$G$_s$T$_s$G$_s$A$_s g_s g_s c_s t_s g_s t_s c_s c_s g_s$a |
| Cur2632 | SEQ ID 109 | 94 | 2256 GM | TGGt$_s g_s a_s g_s g_s c_s t_s g_s t_s$CCGA |
| Cur2633 | SEQ ID 110 | 94 | 2256 GM | TGGt$_s g_s a_s g_s g_s c_s t_s g_s t_s$CCGa |
| Cur2634 | SEQ ID 111 | 91 | 2256 GM | TGGTg$_s a_s g_s g_s c_s t_s g_s t_s$CCGa |
| Cur2635 | SEQ ID 112 | 94 | 2256 WM5 | TGGTGAg$_s g_s c_s t_s g_s t_s c_s c_s g_s$a |
| Cur2412 | SEQ ID 113 | | 2256 GM | TGGT$_s g_s a_s g_s g_s {}^m c_s t_s g_s t_s$CCGA |

(backbone linkage is P = O unless other indicated. s; P = S linkage, small letters; deoxynucleic acid, capital letters; oxy-LNA;).

As shown in Table 2 and FIGS. 1-6, most of SEQ ID NOs 89-104 demonstrated at least 20% inhibition of HIF-1α expression in this experiment and are therefore preferred. The target sites to which these preferred sequences are complementary are herein referred to as "hot spots" and are therefore preferred sites for targeting by compounds of the present invention.

Example 11

In Vivo Efficacy Oligomeric Compounds Targeting HIF-1α

The effect of oligonucleotide treatment on growth of tumour xenografts on nude mice can be measured using different tumour cell lines. Examples of such cell lines are human tumour cell lines U87 (glioblastoma), U373 (glioblastoma), 15PC3 (prostate cancer) and CPH 54A (small cell lung carcinoma) and murine tumour cell line B16 (melanoma).

Treatment of Subcutaneous Tumour Xenografts on Nude Mice Using LNA-Containing Oligos.

Tumour cells were implanted subcutaneously and then serially passaged by three consecutive transplantations. Tumour fragments of 1 mm were implanted subcutaneously with a trocar needle in NMRI nude mice. Alternatively, cancer cells typically $10^6$ cells suspended in 300 μl matrigel (BD Bioscience), were subcutaneously injected into the flanks of NMRI nude mice.

Mice were treated by intra-peritoneal or subcutaneous injection of oligonucleotide at various doses, maximum dose 5 mg/kg/day or by administration of up to 5 mg/kg/day for up to 28 days using ALZET osmotic pumps implanted subcutaneously. Individual treatment of the mice started when tumour volume reached 50 mm$^3$. Treatment with PBS was initiated when mean tumour volume of control group reached 50 mm$^3$. The experiment was terminated when tumours of any group reached maximum allowed sizes. The tumour sizes of all mice were measured daily by caliper measurements. The effect of treatment was measured as tumour size and tumour growth rate. Oligonucleotide treated mice were sacrificed 24 hours after the last oligonucleotide injection.

At the end of treatment period mice were anaesthetised and the tumours were excised and immediately frozen in liquid nitrogen for target analysis.

Results: Mice bearing U373 xenograft tumours were treated with Cur813 (SEQ ID NO 97) 5 mg/kg/day, i.p.×1 daily for 7 days or PBS 100 μl/10 g/day, i.p.×1 daily for 7 days. Five mice were treated in each group. Tumour evaluation was carried out as outlined above. Tumour growth curves are shown in FIG. 9.

Comparison of Tumour Size (T-Test)

| Day | P-value |
|---|---|
| 4 | 0.0477 |
| 5 | 0.0156 |
| 6 | 0.0354 |
| 7 | 0.0461 |

Kaplan Meier Analysis:
Terminal Event: Tumour Size 150 mm$^3$:

| Group No. | Censored | Events | Median survival, days |
|---|---|---|---|
| PBS | 5 | 0 | 5 | 5 |
| Cur813 | 5 | 1 | 4 | 7 |

Logrank test for equality of survival distributions: P = 0.0138

Treatment of Intracranial Tumor Xenografts on Nude Mice Using LNA-Containing Oligos.

Tumour cells are implanted intracranially on NMRI nude mice and oligonucleotide treatment is initiated 1 week after implantation. Mice are treated by intra-peritonal or subcutaneous injection of oligonucleotide at various doses, maximum dose 2 mg/kg or PBS. The number of treatments will depend on the tumour growth rate in the control group. The experiment will be terminated when tumours of any group reach maximum allowed sizes or until death ensues in any group. The effect of treatment will be measured as time until chronic neurological impairment. Oligonucleotide treated mice will be killed 24 hours after the last oligonucleotide injection.

Example 12

In Vivo Analysis

Inhibition of HIF-1α Protein Level in Human Tumour Cells Grown in Vivo Systemic Treatment with Antisense Oligonucleotides The tumours were homogenised in lysis buffer (20 mM Tris-Cl [pH 7.5]; 2% Triton X-100; 1/100 vol. Protease Inhibitor Cocktail Set III (Calbiochem); 1/100 vol. Protease Inhibitor Cocktail Set II (Calbiochem)) at 4° C. with the use of a motor-driven tissue homogeniser. 500 μl lysis buffer is applied per 100 mg tumour tissue. Tumour lysates were centrifuged at 13,000 g for 5 min at 4° C. to remove tissue debris. Protein concentrations of the tumour extracts were determined using the BCA Protein Assay Reagent Kit (Pierce, Rockford). Western blot analysis of target protein expression was carried out as described in example 8.

The present invention has been described with specificity in accordance with certain of its preferred embodiments. Therefore, the following examples serve only to illustrate the invention and are not intended to limit the same.

What is claimed is:

1. A method of treating a mammal suffering from cancer, comprising administering to the mammal a composition comprising a therapeutically effective amount of an oligonucleotide compound targeted to Hif-1alpha and having the base sequence set forth in SEQ ID NO: 3 and an agent selected from the group consisting of an antiinflammatory agent, a corticosteroid, an antiviral agent, a chemotherapeutic agent, and an immuno-modulating agent, wherein the cancer is selected from the group consisting of kidney cancer, melanoma, glioblastoma and prostate cancer, and wherein the oligonucleotide compound comprises one or more LNA units.

2. The method of claim 1, wherein the cancer is kidney cancer.

3. The method of claim 1, wherein the cancer is melanoma.

4. The method of claim 1, wherein the cancer is glioblastoma.

5. The method of claim 1, wherein the cancer is prostate cancer.

6. The method of claim 1, wherein the composition is administered parenterally.

7. The method of claim 1, wherein the composition is administered intravenously.

8. The method of claim 1, wherein the composition is administered by bolus injection into a target organ.

9. The method of claim 1, wherein the composition is administered intraperitoneally.

* * * * *

SEQUENCE LISTING

<160> NUMBER OF SEQ ID NOS: 124

<210> SEQ ID NO 1
<211> LENGTH: 3933
<212> TYPE: DNA
<213> ORGANISM: Homo sapiens

<400> SEQUENCE: 1

```
cacgaggcag cactctcttc gtcgcttcgg ccagtgtgtc gggctgggcc ctgacaagcc    60
acctgaggag aggctcggag ccgggcccgg accccggcga ttgccgcccg cttctctcta   120
gtctcacgag gggtttcccg cctcgcaccc ccacctctgg acttgccttt ccttctcttc   180
tccgcgtgtg gagggagcca gcgcttaggc cggagcgagc ctggggggccg cccgccgtga   240 agacatcgcg gggaccgatt caccatggag ggcgccggcg gcgcgaacga caagaaaaag   300
ataagttctg aacgtcgaaa agaaaagtct cgagatgcag ccagatctcg gcgaagtaaa   360
gaatctgaag ttttttatga gcttgctcat cagttgccac ttccacataa tgtgagttcg   420
catcttgata aggcctctgt gatgaggctt accatcagct atttgcgtgt gaggaaactt   480
ctggatgctg gtgatttgga tattgaagat gacatgaaag cacagatgaa ttgcttttat   540
ttgaaagcct tggatggttt tgttatggtt ctcacagatg atggtgacat gatttacatt   600
tctgataatg tgaacaaata catgggatta actcagtttg aactaactgg acacagtgtg   660
tttgatttta ctcatccatg tgaccatgag gaaatgagag aaatgcttac acacagaaat   720
ggccttgtga aaagggtaa agaacaaaac acacagcgaa gcttttttct cagaatgaag   780
tgtaccctaa ctagccgagg aagaactatg aacataaagt ctgcaacatg gaaggtattg   840
cactgcacag gccacattca cgtatatgat accaacagta accaacctca gtgtgggtat   900
aagaaaccac ctatgacctg cttggtgctg atttgtgaac ccattcctca cccatcaaat   960
attgaaattc ctttagatag caagactttc ctcagtcgac acagcctgga tatgaaattt  1020
tcttattgtg atgaaagaat taccgaattg atgggatatg agccagaaga acttttaggc  1080
cgctcaattt atgaatatta tcatgctttg gactctgatc atctgaccaa aactcatcat  1140
gatatgttta ctaaaggaca agtcaccaca ggacagtaca ggatgcttgc caaaagaggt  1200
ggatatgtct gggttgaaac tcaagcaact gtcatatata acaccaagaa ttctcaacca  1260
cagtgcattg tatgtgtgaa ttacgttgtg agtggtatta ttcagcacga cttgattttc  1320
tcccttcaac aaacagaatg tgtccttaaa ccggttgaat cttcagatat gaaaatgact  1380
cagctattca ccaaagttga atcagaagat acaagtagcc tctttgacaa acttaagaag  1440
gaacctgatg ctttaacttt gctggccca gccgctggag acacaatcat atctttagat  1500
tttggcagca acgacacaga aactgatgac cagcaacttg aggaagtacc attatataat  1560
gatgtaatgc tcccctcacc caacgaaaaa ttacagaata taaatttggc aatgtctcca  1620
ttacccaccg ctgaaacgcc aaagccactt cgaagtagtg ctgaccctgc actcaatcaa  1680
gaagttgcat taaaattaga accaaatcca gagtcactgg aactttcttt taccatgccc  1740
cagattcagg atcagacacc tagtccttcc gatggaagca ctagacaaag ttcacctgag  1800
cctaatagtc ccagtgaata ttgtttttat gtggatagtg atatggtcaa tgaattcaag  1860
ttggaattgg tagaaaaact ttttgctgaa gacacagaag caaagaaccc attttctact  1920
caggacacag atttagactt ggagatgtta gctccctata tcccaatgga tgatgacttc  1980
cagttacgtt ccttcgatca gttgtcacca ttagaaagca gttccgcaag ccctgaaagc  2040
gcaagtcctc aaagcacagt tacagtattc cagcagactc aaatacaaga acctactgct  2100
aatgccacca ctaccactgc caccactgat gaattaaaaa cagtgacaaa agaccgtatg  2160
gaagacatta aaatattgat tgcatctcca tctcctaccc acatacataa agaaactact  2220
agtgccacat catcaccata tagagatact caaagtcgga cagcctcacc aaacagagca  2280
ggaaaaggag tctagaaaca gacagaaaaa tctcatccaa gaagccctaa cgtgttatct  2340
gtcgctttga gtcaaagaac tacagttcct gaggaagaac taaatccaaa gatactagct  2400
```

-continued

```
ttgcagaatg ctcagagaaa gcgaaaaatg aacatgatg gttcacttttt tcaagcagta    2460 ggaattggaa cattattaca gcagccagac gatcatgcag ctactacatc actttcttgg    2520
aaacgtgtaa aaggatgcaa atctagtgaa cagaatggaa tggagcaaaa gacaattatt    2580
ttaataccct ctgatttagc atgtagactg ctggggcaat caatggatga agtggatta    2640 ccacagctga ccagttatga ttgtgaagtt aatgctccta caaggcag cagaaaccta    2700 ctgcagggtg aagaattact cagagctttg gatcaagtta actgagcttt tcttaattt    2760 cattcctttt tttggacact ggtggctcac tacctaaagc agtctattta tattttctac    2820
atctaatttt agaagcctgg ctacaatact gcacaaactt ggttagttca attttttgatc    2880 cccttctac ttaatttaca ttaatgctct tttttagtat gttctttaat gctggatcac    2940
agacagctca ttttctcagt tttttggtat ttaaaccatt gcattgcagt agcatcattt    3000
taaaaaatgc acctttttat ttatttattt ttggctaggg agtttatccc ttttttcgaat    3060 tatttttaag aagatgccaa tataattttt gtaagaaggc agtaacctttt catcatgatc    3120 ataggcagtt gaaaaatttt tacacctttt ttttcacatt ttacataaat aataatgctt    3180
tgccagcagt acgtggtagc cacaattgca caatatattt tcttaaaaaa taccagcagt    3240
tactcatgga atatattctg cgtttataaa actagtttt aagaagaaat ttttttttggc    3300 ctatgaaatt gttaaacctg gaacatgaca ttgttaatca tataataatg attcttaaat    3360
gctgtatggt ttattattta aatgggtaaa gccatttaca taatatagaa agatatgcat    3420
atatctagaa ggtatgtggc atttatttgg ataaaattct caattcagag aaatcatctg    3480
atgtttctat agtcactttg ccagctcaaa agaaaacaat accctatgta gttgtggaag    3540
tttatgctaa tattgtgtaa ctgatattaa acctaaatgt tctgcctacc ctgttggtat    3600
aaagatattt tgagcagact gtaaacaaga aaaaaaaaat catgcattct tagcaaaatt    3660
gcctagtatg ttaatttgct caaaatacaa tgtttgattt tatgcacttt gtcgctatta    3720
acatcctttt tttcatgtag atttcaataa ttgagtaatt ttagaagcat tattttagga    3780
atatatagtt gtcacagtaa atatcttgtt ttttctatgt acattgtaca aattttttcat    3840 tccttttgct ctttgtggtt ggatctaaca ctaactgtat tgttttgtta catcaaataa    3900
acatcttctg tggaaaaaaa aaaaaaaaaa aaa                                3933
```

<210> SEQ ID NO 2
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 2
gcgatgtctt cacggc                                                       16

<210> SEQ ID NO 3
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 3
tggtgaggct gtccga                                                       16

<210> SEQ ID NO 4
<211> LENGTH: 16
<212> TYPE: DNA

```
<213> ORGANISM: Artificial Sequence
<220> FEATURE:
<223> OTHER INFORMATION: Synthetic oligonucleotide

<400> SEQUENCE: 4
atggtgaatc ggtccc                                              16

<210> SEQ ID NO 5
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 5
tggtgaatcg gtcccc                                              16

<210> SEQ ID NO 6
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 6
aggtggcttg tcaggg                                              16

<210> SEQ ID NO 7
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 7
atgtcttcac ggcggg                                              16

<210> SEQ ID NO 8
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 8
cgatgtcttc acggcg                                              16

<210> SEQ ID NO 9
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 9
ggcttgcgga actgct                                              16

<210> SEQ ID NO 10
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 10
ttgtgtctcc agcggc                                              16
```

```
<210> SEQ ID NO 11
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 11
cgaagagagt gctgcc                                                    16

<210> SEQ ID NO 12
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 12
aggcaagtcc agaggt                                                    16

<210> SEQ ID NO 13
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 13
gctaacatct ccaagt                                                    16

<210> SEQ ID NO 14
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 14
gaagtcatca tccatt                                                    16

<210> SEQ ID NO 15
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 15
gtgtctgatc ctgaat                                                    16

<210> SEQ ID NO 16
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 16
atccacataa aaacaa                                                    16

<210> SEQ ID NO 17
<211> LENGTH: 16
<212> TYPE: DNA
<213> ORGANISM: Artificial Sequence
<220> FEATURE:
<223> OTHER INFORMATION: Synthetic oligonucleotide
```

```
<400> SEQUENCE: 17
ctgtaactgt gctttg                                                    16

<210> SEQ ID NO 18
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 18
taggagatgg agatgc                                                    16

<210> SEQ ID NO 19
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 19
cgttagggct tcttgg                                                    16

<210> SEQ ID NO 20
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 20
tccaagaaag tgatgt                                                    16

<210> SEQ ID NO 21
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 21
ccactttcat ccattg                                                    16

<210> SEQ ID NO 22
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 22
ttctgctgcc ttgtat                                                    16

<210> SEQ ID NO 23
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 23
tttaggtagt gagcca                                                    16

<210> SEQ ID NO 24
<211> LENGTH: 16
<212> TYPE: DNA
```

```
<213> ORGANISM: Artificial Sequence
<220> FEATURE:
<223> OTHER INFORMATION: Synthetic oligonucleotide

<400> SEQUENCE: 24
gcagtattgt agccag                                                     16

<210> SEQ ID NO 25
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 25
tattggcatc ttctta                                                     16

<210> SEQ ID NO 26
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 26
tgatgaaagg ttactg                                                     16

<210> SEQ ID NO 27
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 27
ggcaaagcat tattat                                                     16

<210> SEQ ID NO 28
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 28
aaccatacag cattta                                                     16

<210> SEQ ID NO 29
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 29
aataaaccat acagca                                                     16

<210> SEQ ID NO 30
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 30
tgccacatac cttcta                                                     16
```

```
<210> SEQ ID NO 31
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 31
atccaaataa atgcca                                               16

<210> SEQ ID NO 32
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 32
cataaacttc cacaac                                               16

<210> SEQ ID NO 33
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 33
gcggagaaga gaagga                                               16

<210> SEQ ID NO 34
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 34
ccaacagggt aggcag                                               16

<210> SEQ ID NO 35
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 35
aatagcgaca aagtgc                                               16

<210> SEQ ID NO 36
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 36
aaccacaaag agcaaa                                               16

<210> SEQ ID NO 37
<211> LENGTH: 16
<212> TYPE: DNA
<213> ORGANISM: Artificial Sequence
<220> FEATURE:
<223> OTHER INFORMATION: Synthetic oligonucleotide
```

```
<400> SEQUENCE: 37
tttagttctt cctcag                                                   16

<210> SEQ ID NO 38
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 38
accaagtttg tgcagt                                                   16

<210> SEQ ID NO 39
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 39
tttttcgctt tctctg                                                   16

<210> SEQ ID NO 40
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 40
cagcattaaa gaacat                                                   16

<210> SEQ ID NO 41
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 41
aaaatgatgc tactgc                                                   16

<210> SEQ ID NO 42
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 42
tgatccaaag ctctga                                                   16

<210> SEQ ID NO 43
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 43 tcttttttctt gtcgtt                                                  16

<210> SEQ ID NO 44
<211> LENGTH: 16
```

```
<212> TYPE: DNA
<213> ORGANISM: Artificial Sequence
<220> FEATURE:
<223> OTHER INFORMATION: Synthetic oligonucleotide

<400> SEQUENCE: 44
ataaactccc tagcca                                                 16

<210> SEQ ID NO 45
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 45
gtaactgctg gtattt                                                 16

<210> SEQ ID NO 46
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 46
taacaatttc ataggc                                                 16

<210> SEQ ID NO 47
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 47
gctggcaaag tgacta                                                 16

<210> SEQ ID NO 48
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 48
tttacagtct gctcaa                                                 16

<210> SEQ ID NO 49
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 49
cattgtattt tgagca                                                 16

<210> SEQ ID NO 50
<211> LENGTH: 16
<212> TYPE: DNA
<213> ORGANISM: Artificial Sequence
<220> FEATURE:
<223> OTHER INFORMATION: Synthetic
      oligonucleotide
```

```
<400> SEQUENCE: 50
tttactgtga caacta                                                    16

<210> SEQ ID NO 51
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 51
aacaaaacaa tacagt                                                    16

<210> SEQ ID NO 52
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 52
tggcaactga tgagca                                                    16

<210> SEQ ID NO 53
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 53
tcaccagcat ccagaa                                                    16

<210> SEQ ID NO 54
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 54
atcagcacca agcagg                                                    16

<210> SEQ ID NO 55
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 55
tggcaagcat cctgta                                                    16

<210> SEQ ID NO 56
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 56
```

```
tctgtgtcgt tgctgc                                                    16
```

<210> SEQ ID NO 57
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 57

```
tggtggcatt agcagt                                                    16
```

<210> SEQ ID NO 58
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 58

```
catcagtggt ggcagt                                                    16
```

<210> SEQ ID NO 59
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 59

```
tggtgatgat gtggca                                                    16
```

<210> SEQ ID NO 60
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 60

```
tcgtctggct gctgta                                                    16
```

<210> SEQ ID NO 61
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 61

```
ttgctccatt ccattc                                                    16
```

<210> SEQ ID NO 62
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 62

```
aagcgggcgg caatcg                                                    16
```

<210> SEQ ID NO 63
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 63
attctttact tcgccg                                             16

<210> SEQ ID NO 64
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 64
caagatgcga actcac                                             16

<210> SEQ ID NO 65
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 65
attcatctgt gctttc                                             16

<210> SEQ ID NO 66
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 66
tgtcaccatc atctgt                                             16

<210> SEQ ID NO 67
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 67
gcttcgctgt gtgttt                                             16

<210> SEQ ID NO 68
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 68
tgtccagtta gttcaa                                             16

```
<210> SEQ ID NO 69
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 69
tgtgtgtaag catttc                                                    16

<210> SEQ ID NO 70
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 70
gcagacttta tgttca                                                    16

<210> SEQ ID NO 71
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 71
gttggttact gttggt                                                    16

<210> SEQ ID NO 72
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 72
ttgctatcta aaggaa                                                    16

<210> SEQ ID NO 73
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 73
atcagagtcc aaagca                                                    16

<210> SEQ ID NO 74
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 74
gttcttctgg ctcata                                                    16

<210> SEQ ID NO 75
<211> LENGTH: 16
```

```
<212> TYPE: DNA
<213> ORGANISM: Artificial Sequence
<220> FEATURE:
<223> OTHER INFORMATION: Synthetic
      oligonucleotide

<400> SEQUENCE: 75
atttcatatc caggct                                                     16

<210> SEQ ID NO 76
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 76
tactgtcctg tggtga                                                     16

<210> SEQ ID NO 77
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 77
tatgacagtt gcttga                                                     16

<210> SEQ ID NO 78
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 78
aataccactc acaacg                                                     16

<210> SEQ ID NO 79
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 79
tctgtttgtt gaaggg                                                     16

<210> SEQ ID NO 80
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 80
aactttggtg aatagc                                                     16

<210> SEQ ID NO 81
<211> LENGTH: 16
<212> TYPE: DNA
<213> ORGANISM: Artificial Sequence
```

<220> FEATURE:
<223> OTHER INFORMATION: Synthetic
      oligonucleotide

<400> SEQUENCE: 81
taaagcatca ggttcc                                                   16

<210> SEQ ID NO 82
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 82
gggagcatta catcat                                                   16

<210> SEQ ID NO 83
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 83
gtgggtaatg gagaca                                                   16

<210> SEQ ID NO 84
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 84
cttcttgatt gagtgc                                                   16

<210> SEQ ID NO 85
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 85
gtgactctgg atttgg                                                   16

<210> SEQ ID NO 86
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 86
caggtgaact ttgtct                                                   16

<210> SEQ ID NO 87
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 87
attcactggg actatt                                                          16

<210> SEQ ID NO 88
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 88
tgcttctgtg tcttca                                                          16

<210> SEQ ID NO 89
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 89
gcgatgtctt cacggc                                                          16

<210> SEQ ID NO 90
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 90
gcgatgtctt cacggc                                                          16

<210> SEQ ID NO 91
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 91
gcgatgtctt cacggc                                                          16

<210> SEQ ID NO 92
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 92
gcgatgtctt cacggc                                                          16

<210> SEQ ID NO 93
<211> LENGTH: 16
<212> TYPE: DNA
<213> ORGANISM: Artificial Sequence
<220> FEATURE:
<223> OTHER INFORMATION: Synthetic
      oligonucleotide

```
<400> SEQUENCE: 93
gcgatgtctt cacggc                                                    16

<210> SEQ ID NO 94
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 94
gcgatgtctt cacggc                                                    16

<210> SEQ ID NO 95
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 95
tggtgaggct gtccga                                                    16

<210> SEQ ID NO 96
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 96
tggtgaggct gtccga                                                    16

<210> SEQ ID NO 97
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 97
tggtgaggct gtccga                                                    16

<210> SEQ ID NO 98
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 98
tggtgaggct gtccga                                                    16

<210> SEQ ID NO 99
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 99
```

-continued tggtgaggct gtccga                                                  16

<210> SEQ ID NO 100
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 100
tggtgaggct gtccga                                                  16

<210> SEQ ID NO 101
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 101
gcgatctctt cagggc                                                  16

<210> SEQ ID NO 102
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 102
gcgttgtcat cacggc                                                  16

<210> SEQ ID NO 103
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 103
tggtgagcct gtcgga                                                  16

<210> SEQ ID NO 104
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 104
tgctgagggt gtccga                                                  16

<210> SEQ ID NO 105
<211> LENGTH: 16
<212> TYPE: DNA
<213> ORGANISM: Artificial Sequence
<220> FEATURE:
<223> OTHER INFORMATION: Synthetic
      oligonucleotide

<400> SEQUENCE: 105
tggtgaggct gtccga                                                  16

<210> SEQ ID NO 106
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 106
tggtgaggct gtccga                                                     16

<210> SEQ ID NO 107
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 107
tggtgaggct gtccga                                                     16

<210> SEQ ID NO 108
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 108
tggtgaggct gtccga                                                     16

<210> SEQ ID NO 109
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 109
tggtgaggct gtccga                                                     16

<210> SEQ ID NO 110
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 110
tggtgaggct gtccga                                                     16

<210> SEQ ID NO 111
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 111
tggtgaggct gtccga                                                     16

<210> SEQ ID NO 112

-continued

<210> SEQ ID NO 112
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 112
tggtgaggct gtccga                                                 16

<210> SEQ ID NO 113
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 113
tggtgaggct gtccga                                                 16

<210> SEQ ID NO 114
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 114
gttactgcct tcttac                                                 16

<210> SEQ ID NO 115
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 115
ccggcgccct ccatgg                                                 16

<210> SEQ ID NO 116
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 116
ctcatccaag aagccctaac gtgtt                                       25

<210> SEQ ID NO 117
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 117
gctttctctg agcattctgc aaagc                                       25

<210> SEQ ID NO 118
<211> LENGTH: 35
<212> TYPE: DNA

<213> ORGANISM: Artificial Sequence
<220> FEATURE:
<223> OTHER INFORMATION: Synthetic oligonucleotide

<400> SEQUENCE: 118
cctcaggaac tgtagttctt tgactcaaag cgaca                                35

<210> SEQ ID NO 119
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 119
gccggcgccc tccat                                                      15

<210> SEQ ID NO 120
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 120
tcttctcgtt ctcgcc                                                     16

<210> SEQ ID NO 121
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 121
cctccatggc gaatcggtgc                                                 20

<210> SEQ ID NO 122
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 122
aaggctgtgg gcaaggtcat c                                               21

<210> SEQ ID NO 123
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 123
gtcagatcca cgacggacac att                                             23

<210> SEQ ID NO 124
<211> LENGTH: 34
<212> TYPE: DNA
<213> ORGANISM: Artificial Sequence
<220> FEATURE:

```
<223> OTHER INFORMATION: Synthetic
      oligonucleotide

<400> SEQUENCE: 124
gaagctcact ggcatggcat ggccttccgt gttc                              34
```